US007514421B2

(12) United States Patent
Abrahamsson et al.

(10) Patent No.: US 7,514,421 B2
(45) Date of Patent: Apr. 7, 2009

(54) USE OF AN IBAT INHIBITOR FOR THE TREATMENT OF CONSTIPATION

(75) Inventors: Hasse Roland Abrahamsson, Gotenborg (SE); Per-Goran Gillberg, Molndal (SE)

(73) Assignee: Albireo AB, Gothenburg (SE)

( * ) Notice: Subject to any disclaimer, the term of this patent is extended or adjusted under 35 U.S.C. 154(b) by 0 days.

(21) Appl. No.: 10/551,999

(22) PCT Filed: Apr. 1, 2004

(86) PCT No.: PCT/GB2004/001396

§ 371 (c)(1),
(2), (4) Date: Oct. 4, 2005

(87) PCT Pub. No.: WO2004/089350

PCT Pub. Date: Oct. 21, 2004

(65) Prior Publication Data

US 2006/0199797 A1  Sep. 7, 2006

(30) Foreign Application Priority Data

Apr. 5, 2003  (GB) ................................. 0307918.3

(51) Int. Cl.
*A61K 31/554* (2006.01)
(52) U.S. Cl. ................................. 514/211.09; 514/211.1
(58) Field of Classification Search ........................ None
See application file for complete search history.

(56) References Cited

U.S. PATENT DOCUMENTS

| 6,906,058 | B2 | 6/2005 | Starke et al. | 514/211.1 |
| 7,132,557 | B2 * | 11/2006 | Wilkes et al. | 556/413 |
| 2002/0142054 | A1 | 10/2002 | Marlett et al. | 424/738 |
| 2005/0124557 | A1 * | 6/2005 | Lindqvist | 514/23 |

FOREIGN PATENT DOCUMENTS

| DE | 19825804 | 8/2000 |
| EP | 0372542 | 10/1992 |
| EP | 0864582 | 9/1998 |
| GB | 2262888 | 7/1996 |
| WO | WO 93/16055 | 8/1993 |
| WO | WO 94/18183 | 8/1994 |
| WO | WO 94/18184 | 8/1994 |
| WO | WO 96/05188 | 2/1996 |
| WO | WO 96/08484 | 3/1996 |
| WO | WO 96/16051 | 5/1996 |
| WO | WO 97/33882 | 9/1997 |
| WO | WO 98/38182 | 9/1998 |
| WO | WO 98/40375 | 9/1998 |
| WO | WO 99/01149 | 1/1999 |
| WO | WO 99/32478 | 7/1999 |
| WO | WO 99/35135 | 7/1999 |
| WO | WO 99/64409 | 12/1999 |
| WO | WO 99/64410 | 12/1999 |
| WO | WO 00/01687 | 1/2000 |
| WO | WO 00/38725 | 7/2000 |
| WO | WO 00/38726 | 7/2000 |
| WO | WO 00/38727 | 7/2000 |
| WO | WO 00/38728 | 7/2000 |
| WO | WO 00/38729 | 7/2000 |
| WO | WO 00/47568 | 8/2000 |
| WO | WO 00/61568 | 10/2000 |
| WO | WO 00/62810 | 10/2000 |
| WO | WO 01/60807 | 8/2001 |
| WO | WO 01/66533 | 9/2001 |
| WO | WO 01/68096 | 9/2001 |
| WO | WO 01/68637 | 9/2001 |
| WO | WO 02/08211 | 1/2002 |
| WO | WO 02/32428 | 4/2002 |
| WO | WO 02/50051 | 6/2002 |
| WO | WO 02/53548 | 7/2002 |
| WO | WO 03/020710 | 3/2003 |
| WO | WO 03/022286 | 3/2003 |
| WO | WO 03/022825 | 3/2003 |
| WO | WO 03/022830 | 3/2003 |
| WO | WO 03/061663 | 7/2003 |
| WO | WO 03/091232 | 11/2003 |
| WO | WO 03/106482 | 12/2003 |
| WO | WO 2004/006899 | 1/2004 |
| WO | WO 2004/076430 | 9/2004 |

OTHER PUBLICATIONS

Govers et al. "Characterization of the adsorption of conjugated and unconjugated bile acids to insoluble, amorphous calcium phosphate" Journal of Lipid Research 35(5):741-748 (1994).
Higaki et al. "Inhibition of ileal Na+/bile acid cotransporter by S-8921 reduces serum cholesterol and prevents atherosclerosis in rabbits" Arteriosclerosis, Thrombosis, and Vascular Biology 18(8):1304-1311 (1998).
Ishibashi et al. "Hypercholesterolemia in low density lipoprotein receptor knockout mice and its reversal by adenovirus-mediated gene delivery" Journal of Clinical Investigation 92(2):883-893 (1993).
Plump et al. "Severe hypercholesterolemia and atherosclerosis in apolipoprotein E-deficient mice created by homologous recombination in ES cells" Cell (71):343-353 (1992).
Schiller "Review article: the therapy of constipation" Alimentary Pharmacology and Therapeutics 15(6):749-763 (2001).
Sprong et al. "Dietary Calcium Phosphate Promotes Listeria monocytogenes Colonization and Translocation in Rats Fed Diets Containing Corn Oil but Not Milk Fat1" J. Nutrition (US) 132(6):1269-1274 (2002).
Van Tilburg et al. "Na+-dependent bile acid transport in the ileum: the balance between diarrhea and constipation" Gastroenterology 98(1):25-32 (1989).
Welberg et al. "Calcium and the prevention of colon cancer" Scandinavian J. Gastroenterology Suppl. 188: 52-59 (1991).
Lewis et al., (1995) "Effects of 2164U90 on ileal bile acid absorption and serum cholesterol in rats and mice" Journal of Lipid Research, 36(5): 1098-1105.

* cited by examiner

*Primary Examiner*—Phyllis G. Spivack
(74) *Attorney, Agent, or Firm*—Fish & Richardson P.C.

(57) ABSTRACT

A method of treatment of functional constipation or C-IBS in a warm-blooded animal is disclosed, which comprises the administration of an IBAT inhibitor.

4 Claims, No Drawings

USE OF AN IBAT INHIBITOR FOR THE TREATMENT OF CONSTIPATION

The present invention relates to a novel treatment and/or prophylaxis of functional constipation and constipation predominant Irritable Bowel Syndrome (C-IBS). More specifically the invention relates to the use of an ileal bile acid transport (IBAT) inhibitor in the treatment and/or prophylaxis of these disorders and pharmaceutical compositions comprising said IBAT inhibitor for use in the treatment and/or prophylaxis of these disorders.

Constipation and/or its associated symptoms, afflicts many people in the Western World and the prevalence is greatest amongst children and the elderly. Constipation can occur in up to 20% of a population depending on the demographic factors, sampling and definitions used. In a study of approximately 2000 people in five different European countries (Gastroenterology 118:A720, 2000), between 6% and 23% of subjects said that they had experienced constipation during the past 12 months, approximately 20% of the subjects had taken a laxative within that period and at least 10% experienced difficulty in defecation at least once a month. In the 1991 National Health Interview Survey, about 4.5 million people in the United States say they are constipated most or all of the time. Those reporting constipation most often are women, children, and adults age 65 and over. Pregnant women also complain of constipation, and it is a common problem following childbirth or surgery. Females constitute the largest group of patients with constipation and the problem increases with age in most studies.

Surveys of Western populations have revealed IBS in 15-20% of adolescents and adults, with a higher prevalence in women (the prevalence is variable in other populations). 30 to 35% of IBS patients have constipation as a major symptom together with abdominal pain and/or discomfort (C-IBS).

Causes of constipation are varied and include general factors such as sex, age, nationality, diet and exercise; colonic anatomy and function such as luminal contents, absorption of water and sodium, diameter and length of the colon and colonic motor function; defecatory function such as normal defunction, failure of relaxation of the anal sphincter complex, ineffective straining, diminished rectal sensation and size and consistency of stool; disorders of the anorectum and pelvic floor; and psychological and behavioural factors. Some medical conditions can cause or result in constipation, for example neurological disorders such as multiple sclerosis, Parkinson's disease; chronic idiopathic intestinal pseudo-obstruction; stroke and spinal cord injuries; metabolic and endocrine conditions such as diabetes, underactive or overactive thyroid gland and uremia; and systemic disorders such as amyloidosis, lupus and scleroderma. Some drug treatments including analgesics such as opiates, anticholinergenics, such as antispasmodics, tricyclic antidepressants, phenothiazolines and antimuscarinics; seretonin receptor antagonists; and calcium/aluminium containing antacids can also cause constipation.

Functional constipation comprises a group of functional disorders which present as persistent difficult, infrequent or seemingly incomplete defecation. It is more common in women and is usually found to increase with age.

IBS comprises a group of functional bowel disorders in which abdominal discomfort or pain is associated with defecation or a change in bowel habit, and with features of disordered defecation. IBS has a chronic relapsing course and overlaps with other functional gastrointestinal disorders. It accounts for high direct medical expenses and indirect costs, including absenteeism from work.

Symptoms associated with constipation include infrequent stools, no urge to pass stools, stools that are difficult to pass, ineffective straining, need to digitate, sense of incomplete evacuation, anal or perineal pain, prolapse at the anus and soiling of clothes. Bloating (distension), discomfort and pain are also symptoms of constipation. When pain is a symptom of constipation it can be caused by various factors including strong contractions and distension of the intestinal tract. There also, seems to be a correlation between high amplitude propagating contractions and pain in constipated patients (Dig Dis Sci 36, 827-862, 1991). Antispasmodics are sometimes used to alleviate this pain because they are believed to reduce strong contractions associated with pain (Pharmacol. Ther., 80, 49-98, 1998). The antimuscarinic compounds atropine (Digestive Diseases & Sciences 40 (6):1381-7, 1995) and zamifenacin (Aliment. Pharmacol. Ther., 11, 561-8, 1997) have both been found to reduce constipation pain.

Current treatment regimes for constipation itself include: (i) dietary fibre; (ii) other bulk laxatives such as psyllium, methylcellulose, and calcium polycarbophil; (iii) polyethelene glycol solution (PEG); (iv) stimulant laxatives such as bisacodyl, sodium picosulphate, or sennosides; (v) 5-hydroxytryptamine 4 (5-HT4) agonists such as prucalopride (vi) enemas and suppositories; and (vii) surgery; but the therapeutic results of these treatments are often disappointing and they can result in unpleasant side effects. For instance, an increase in dietary fibre often doesn't relieve the constipation and in some cases actually worsens the symptoms, for example by aggravating the sense of distension (Gut 27:41, 1986). The other bulk laxatives often fail for the same reason and in general bulk laxatives are only suitable for long term use, they are not appropriate for the rapid relief of temporary constipation. The use of PEG solutions can be effective, but generally involve drinking large volumes of fluid (circa one litre per day for up to three days) which, as well as being unpleasant, is clearly unsuitable for patients, e.g. children, who have difficulty in drinking such amounts. Stimulant laxative treatments have many documented side effects and can result in laxative dependence and abuse. The 5-HT4 agonists, as well as having the desired effect in the colon, can affect gastric emptying and the small bowel (Clinical Pharmacology & Therapeutics, 67:2 (PII-33), 2000). resulting in diarrhea. Enemas and suppositories can result in serious damage to the rectal mucosa, furthermore if large volumes are used in an enema then serious water intoxication can occur if the enema is retained. Surgery, for example a colostomy, can be effective, but has also been documented to give unsatisfactory results, for example further surgery might be needed, the constipation may persist or diarrhea with incontinence may develop.

The laxative effect of bile acids has also been documented (Br J Surg 1979; 66; 776-9; Gut 1975, 16, 894-902; and Gut 1973, 14, 348-353) and although it is feasible to administer bile acids orally for treatment of constipation (Myo Clinic Proceedings, 1973, 48, 356) they have an unwanted effect on the small bowel where they increase the motility—which potentially results in side effects like reduced absorption of nutrients.

There is clearly a need to identify additional treatments for constipation and preferably more effective treatments or ones with reduced side effects.

Many IBAT inhibitors have been disclosed in the literature (see below) and they are identified as being useful in the treatment of dyslipidaemic conditions and disorders, for example hyperlipidaemia, and as useful in the prevention and treatment of different cardiovascular clinical conditions, for example atherosclerosis. The rationale for treatment of a dyslipidaemic condition with an IBAT inhibitor is that by increasing bile acid and cholesterol excretion, a favorable negative cholesterol balance and an improvement to the atherogenic lipoprotein profile should be achieved.

The use of an IBAT inhibitor to treat gastrointestinal (GI) disorders has not been suggested or contemplated in the literature. In fact some reports suggest that therapeutic treatment of dyslipidaemia with an IBAT inhibitor might actually cause GI problems, for example Glaxo SmithKline published a clinical study (abstract, DALM September 2001) showing GI side effects (diarrhea and abdominal cramping) during IBAT inhibition in man.

The present invention concerns a novel treatment and/or prophylaxis of constipation with an IBAT inhibitor. This treatment and/or prophylaxis results in the delivery of bile acids into the colon where they act as endogenous laxatives. Local delivery to the colon avoids the side effects (detailed above) of orally delivering bile acids since they will not affect parts of the GI tract before the colon. Avoiding affecting the GI tract above the colon, by administering an IBAT inhibitor would also be expected to give advantages over treatments with existing pharmaceuticals such as 5-HT4 agonists. In addition, some IBAT inhibitors have very low bioavailability (<2%), in this case the systemic exposure is low resulting in a reduced risk of side effects. Furthermore, IBAT inhibitors could alleviate the pain symptoms by a similar secondary mechanism to antimuscarinic drugs. This alleviation of pain would arise because IBAT inhibitors would increase motility and the amount of water in the content of the lower bowel. This in turn would lead to a softer content that is easier to move and does not accumulate, therefore there would be less distension of the intestine wall and it is well known that distension of the intestinal tract generates pain. Furthermore, fewer high amplitude propagating contractions are needed to move the content of the intestine, when the bowel content are soft, and again less pain is experienced.

Accordingly the present invention comprises the use of an IBAT inhibitor, or a pharmaceutically acceptable salt, solvate, solvate of such a salt or a prodrug thereof, in the treatment and/or prophylaxis of constipation.

Herein where the term "constipation" is used, it is to be understood that this term, unless otherwise qualified, relates to functional constipation and C-IBS. In one aspect of the invention "constipation" relates to functional constipation. In another aspect of the invention "constipation" relates to C-IBS.

One aspect of the invention relates to the treatment of constipation. Another aspect relates to the prophylaxis of constipation. A third aspect relates to the treatment and prophylaxis of constipation.

In one aspect of the invention, where the treatment of constipation is referred to and the constipation relates to C-IBS it is to be understood that this includes alternating (constipation-diarrohea) irritable bowel syndrome.

Also herein, where the terms "functional constipation" and "C-IBS" are used, it is to be understood that they are defined according to the "Rome 2 Criteria" (Gut 45 (Suppl 2): 43, 1999, II43- II47).

In the literature IBAT inhibitors are often referred to by different names. It is to be understood that where IBAT inhibitors are referred to herein, this term also encompasses compounds known in the literature as:
i) ileal apical sodium co-dependent bile acid transporter (ASBT) inhibitors;
ii) bile acid transporter (BAT) inhibitors;
iii) ileal sodium/bile acid cotransporter system inhibitors;
iv) apical sodium-bile acid cotransporter inhibitors;
v) ileal sodium-dependent bile acid transport inhibitors;
vi) bile acid reabsorption (BARI's) inhibitors; and
vii) sodium bile acid transporter (SBAT) inhibitors;

where they act by inhibition of IBAT.

Suitable compounds possessing IBAT inhibitory activity have been described, see for instance the compounds described in WO 93/16055, WO 94/18183, WO 94/18184, WO 94/24087, WO 96/05188, WO 96/08484, WO 96/16051, WO 97/33882, WO 98/07749, WO 98/38182, WO 98/40375, WO 98/56757, WO 99/32478, WO 99/35135, WO 99/64409, WO 99/64410, WO 00/01687, WO 00/20392, WO 00/20393, WO 00/20410, WO 00/20437, WO 01/34570, WO 00/35889, WO 00/47568, WO 00/61568, WO 01/68637, WO 01/68096, WO 02/08211, WO 00/38725, WO 00/38726, WO 00/38727, WO 00/38728, WO 00/38729, DE 19825804, JP 10072371, U.S. Pat. No. 5,070,103, EP 251 315, EP 417 725, EP 489 423, EP 549 967, EP 573 848, EP 624 593, EP 624 594, EP 624 595, EP 869 121, EP 864 582, and EP 1 070 703, and the contents of these patent applications, particularly the compounds described in claim 1 and the named examples, are incorporated herein by reference.

Particular classes of IBAT inhibitors suitable for use in the present invention are benzothiepines. Other suitable classes of IBAT inhibitors are any one of the 1,2-benzothiazepines, 1,4-benzothiazepines and 1,5-benzothiazepines. A further suitable class of IBAT inhibitors is the 1,2,5-benzothiadiazepines.

One particular suitable compound possessing IBAT inhibitory activity is (3R,5R)-3 -butyl-3-ethyl-1,1-dioxido-5-phenyl-2,3,4,5-tetrahydro- 1,4-benzothiazepin-8-yl☐-D-glucopyranosiduronic acid (EP 864 582).

A further suitable compound possessing IBAT inhibitory activity is S-8921 (EP 597 107).

A further suitable IBAT inhibitor is the compound:

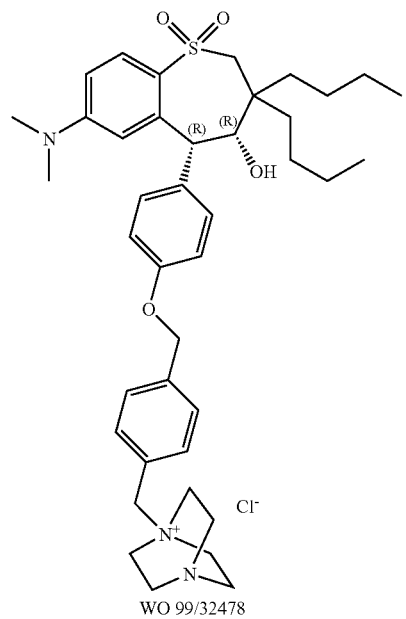

WO 99/32478

Other suitable compounds of the invention are the IBAT inhibitors described in WO 01/66533. A particular compound of the invention is selected from any one of Example 1-39 of WO 01/66533, or a pharmaceutically acceptable salt, solvate, solvate of such a salt or a prodrug thereof, and the compounds of Examples 1-39 are incorporated herein by reference. Claims 1-6 of WO 01/66533 are also incorporated herein by reference.

Additional suitable compounds of the invention are the IBAT inhibitors described in WO 02/50051. A particular compound of the invention is selected from any one of Example 1-120 of WO 02/50051, or a pharmaceutically acceptable salt, solvate, solvate of such a salt or a prodrug thereof, and the compounds of Examples 1-120 are incorporated herein by reference. Claims 1-14 of WO 02/50051 are also incorporated herein by reference. A particular compound of the invention selected from WO 02/50051 is selected from any one of:

1,1-dioxo-3,3-dibutyl-5-phenyl-7-methylthio-8-(N-{(R)-1'-phenyl-1'-[N'-(carboxymethyl) carbamoyl] methyl}carbamoylmethoxy)-2,3,4,5-tetrahydro-1,5-benzothiazepine;

1,1-dioxo-3,3-dibutyl-5-phenyl-7-methylthio-8-(N-{(R)-α-[N'-(carboxymethyl)carbamoyl]-4-hydroxybenzyl}carbamoylmethoxy)-2,3,4,5-tetrahydro-1,5-benzothiazepine;

1,1-dioxo-3,3-dibutyl-5-phenyl-7-methylthio-8-(N-{(R)-1'-phenyl-1'-[N'-(2-sulphoethyl)carbamoyl] methyl}carbamoylmethoxy)-2,3,4,5-tetrahydro-1,5-benzothiazepine;

1,1-dioxo-3-butyl-3-ethyl-5-phenyl-7-methylthio-8-(N-{(R)-1'-phenyl-1'-[N'-(2-sulphoethyl)carbamoyl] methyl}carbamoylmethoxy)-2,3,4,5-tetrahydro-1,5-benzothiazepine;

1,1-dioxo-3,3-dibutyl-5-phenyl-7-methylthio-8-(N-{(R)-α-[N'-(2-sulphoethyl)carbamoyl]4-hydroxybenzyl}carbamoylmethoxy)-2,3,4,5-tetrahydro-1,5-benzothiazepine;

1,1-dioxo-3-butyl-3-ethyl-5-phenyl-7-methylthio-8-(N-{(R)-α-[N'-(2-sulphoethyl) carbamoyl]-4-hydroxybenzyl}carbamoylmethoxy)-2,3,4,5-tetrahydro-1,5-benzothiazepine;

1,1-dioxo-3-butyl-3-ethyl-5-phenyl-7-methylthio-8-(N-{(R)-α-[N'-(2-carboxyethyl)carbamoyl] benzyl}carbamoylmethoxy)-2,3,4,5-tetrahydro-1,5-benzothiazepine;

1,1-dioxo-3,3-dibutyl-5-phenyl-7-methylthio-8-(N-{(R)-α-[N'-(2-carboxyethyl)carbamoyl]-4-hydroxybenzyl}carbamoylmethoxy)-2,3,4,5-tetrahydro-1,5-benzothiazepine;

1,1-dioxo-3-butyl-3-ethyl-5-phenyl-7-methylthio-8-(N-{(R)-α-[N'-(5-carboxypentyl) carbamoyl] benzyl}carbamoylmethoxy)-2,3,4,5-tetrahydro-1,5-benzothiazepine;

1,1-dioxo-3,3-dibutyl-5-phenyl-7-methylthio-8-(N-{(R)-α-[N'-(2-carboxyethyl)carbamoyl] benzyl}carbamoylmethoxy)-2,3,4,5-tetrahydro-1,5-benzothiazepine;

1,1-dioxo-3,3-dibutyl-5-phenyl-7-methylthio-8-(N-{α-[N'-(2-sulphoethyl)carbamoyl]-2-fluorobenzyl}carbamoylmethoxy)-2,3,4,5-tetrahydro-1,5-benzothiazepine;

1,1-dioxo-3-butyl-3-ethyl-5-phenyl-7-methylthio-8-(N-{(R)-α-[N'-(R)-(2-hydroxy-1-carboxyethyl)carbamoyl] benzyl}carbamoylmethoxy)-2,3,4,5-tetrahydro-1,5-benzothiazepine;

1,1-dioxo-3,3-dibutyl-5-phenyl-7-methylthio-8-(N-{(R)-α-[N'-(R)-(2-hydroxy-1-carboxyethyl)carbamoyl] benzyl}carbamoylmethoxy)-2,3,4,5-tetrahydro-1,5-benzothiazepine;

1,1-dioxo-3,3-dibutyl-5-phenyl-7-methylthio-8-{N-[(R)-α-(N'-{(R)-1-[N''-(R)-(2-hydroxy-1-carboxyethyl)carbamoyl]-2-hydroxyethyl}carbamoyl)benzyl]carbamoylmethoxy}-2,3,4,5-tetrahydro-1,5-benzothiazepine;

1,1-dioxo-3-butyl-3-ethyl-5-phenyl-7-methylthio-8-(N-{α-[N'-(carboxymethyl)carbamoyl] benzyl}carbamoylmethoxy)-2,3,4,5-tetrahydro-1,5-benzothiazepine;

1,1-dioxo-3-butyl-3-ethyl-5-phenyl-7-methylthio-8-(N-{α-[N'-((ethoxy)(methyl) phosphoryl-methyl) carbamoyl] benzyl}carbamoylmethoxy)-2,3,4,5-tetrahydro-1,5-benzothiazepine;

1,1-dioxo-3-butyl-3-ethyl-5-phenyl-7-methylthio-8-{N-[(R)-α-(N'-{2-[(hydroxy)(methyl)phosphoryl] ethyl}carbamoyl)benzyl]carbamoylmethoxy}-2,3,4,5-tetrahydro-1,5-benzothiazepine;

1,1-dioxo-3,3-dibutyl-5-phenyl-7-methylthio-8-(N-{(R)-α-[N'-(2-methylthio-1-carboxyethyl)carbamoyl] benzyl}carbamoylmethoxy)-2,3,4,5tetrahydro-1,5-benzothiazepine;

1,1-dioxo-3,3-dibutyl-5-phenyl-7-methylthio-8-{N-[(R)-α-(N'-{2-[(methyl)(ethyl) phosphoryl]ethyl}carbamoyl) 4hydroxybenzyl]carbamoylmethoxyl}-2,3,4,5-tetrahydro-1,5-benzothiazepine;

1,1-dioxo-3,3-dibutyl-5-phenyl-7-methylthio-8-{N-[(R)-α-(N'-{2-[(methyl)(hydroxy) phosphoryl]ethyl}carbamoyl)-4-hydroxybenzyl]carbamoylmethoxy}-2,3,4,5-tetrahydro-1,5-benzothiazepine;

1,1-dioxo-3,3-dibutyl-5-phenyl-7-methylthio-8-(N-{(R)-α-[(R)-N'-(2-methylsulphinyl-1-carboxyethyl)carbamoyl] benzyl}carbamoylmethoxy)-2,3,4,5-tetrahydro-1,5-benzothiazepine; and 1,1-dioxo-3,3-dibutyl-5-phenyl-7-methoxy-8-[N-{(R)-α-[N'-(2-sulphoethyl)carbamoyl]-4-hydroxybenzyl}carbamoylmethoxy]-2,3,4,5-tetrahydro-1,5-benzothiazepine;

or a pharmaceutically acceptable salt, solvate, solvate of such a salt or a prodrug thereof.

Additional suitable compounds of the invention are the IBAT inhibitors described in WO 03/020710. A particular compound of the invention is selected from any one of Example 1-44 of WO 03/020710, or a pharmaceutically acceptable salt, solvate, solvate of such a salt or a prodrug thereof, and the compounds of Examples 1-44 are incorporated herein by reference. Claims 1-10 of WO 03/020710 are also incorporated herein by reference. A particular compound of the invention selected from WO 03/020710 is selected from any one of:

1,1-dioxo-3,3-dibutyl-5-phenyl-7-methylthio-8-(N-{(R)-α-[N'-(2-(S)-3-(R)-4-(R)-5-(R)-2,3,4,5,6-pentahydroxyhexyl)carbamoyl]benzyl}carbamoylmethoxy)-2,3,4,5-tetrahydro-1,5-benzothiazepine;

1,1-dioxo-3-butyl-3-ethyl-5-phenyl-7-methylthio-8-(N-{(R)-α-[N'-(2-(S)-3-(R)-4-(R)-5-----(R) -2,3,4,5,6-pentahydroxyhexyl)carbamoyl]benzyl}carbamoylmethoxy)-2,3,4,5-tetrahydro-1,5-benzothiazepine;

1,1-dioxo-3-butyl-3-ethyl-5-phenyl-7-methylthio-8-(N-{(R)-α-[N'-((S)-1-carbamoyl-2-hydroxyethyl)carbamoyl] benzyl}carbamoylmethoxy)-2,3,4,5-tetrahydro-1,5-benzothiazepine;

1,1-dioxo-3-butyl-3-ethyl-5-phenyl-7-methylthio-8-(N-{(R)-α-[N'-(hydroxycarbamoyl-methyl) carbamoyl] benzyl}carbamoylmethoxy)-2,3,4,5-tetrahydro-1,5-benzothiazepine;

1,1-dioxo-3-butyl-3-ethyl-5-phenyl-7-methylthio-8-[N-((R)-α-{N'-[2-(N'-pyrimidin-2-ylureido)ethyl] carbamoyl}benzyl)carbamoylmethoxy]-2,3,4,5-tetrahydro-1,5-benzothiazepine;

1,1-dioxo-3-butyl-3-ethyl-5-phenyl-7-methylthio-8-[N-((R)-α-{N'-[2-(N'-pyridin-2-ylureido)ethyl]carbamoyl}benzyl)carbamoylmethoxy]-2,3,4,5-tetrahydro-1,5-benzothiazepine;

1,1-dioxo-3-butyl-3-ethyl-5-phenyl-7-methylthio-8-(N-{(R)-α-[N'-(1-t-butoxycarbonylpiperidin-4-ylmethyl)carbamoyl]benzyl}carbamoylmethoxy)-2,3,4,5-tetrahydro-1,5-benzothiazepine;

1,1-dioxo-3-butyl-3-ethyl-5-phenyl-7-methylthio-8-(N-{(R)-α-[N'-(2,3-dihydroxypropyl)carbamoyl]benzyl}carbamoylmethoxy)-2,3,4,5-tetrahydro-1,5-benzothiazepine;

1,1-dioxo-3-butyl-3-ethyl-5-phenyl-7-methylthio-8-[N-((R)-α-{N'-[2-(3,4-dihydroxyphenyl)-2-methoxyethyl]carbamoyl}benzyl)carbamoylmethoxy]-2,3,4,5-tetrahydro-1,5-benzothiazepine 1,1-dioxo-3-butyl-3-ethyl-5-phenyl-7-methylthio-8-(N-{(R)-α-[N'-(2-aminoethyl)carbamoyl]benzyl}carbamoylmethoxy)-2,3,4,5-tetrahydro-1,5-benzothiazepine;

1,1-dioxo-3-butyl-3-ethyl-5-phenyl-7-methylthio-8-(N-{(R)-α-[N'-(piperidin-4-ylmethyl) carbamoyl]benzyl}carbamoylmethoxy)-2,3,4,5-tetrahydro-1,5-benzothiazepine; or 1,1-dioxo-3-butyl-3-ethyl-5-phenyl-7-methylthio-8-(N-{(R)-α-[N'-(2-N,N-dimethylaminosulphamoylethyl)carbamoyl]benzyl}carbamoylmethoxy)-2,3,4,5-tetrahydro-1,5-benzothiazepine;

or a pharmaceutically acceptable salt, solvate, solvate of such a salt or a prodrug thereof.

Additional suitable compounds of the invention are the IBAT inhibitors described in WO 03/022825. A particular compound of the invention is selected from any one of Example 1-7 of WO 03/022825, or a pharmaceutically acceptable salt, solvate, solvate of such a salt or a prodrug thereof, and the compounds of Examples 1-7 are incorporated herein by reference. Claims 1-8 of WO 03/022825 are also incorporated herein by reference. A particular compound of the invention selected from WO 03/022825 is selected from any one of:

1,1-dioxo-3(R)-3-butyl-3-ethyl-5-(R)-5-phenyl-8-[N-((R)-α-carboxybenzyl) carbamoylmethoxy]-2,3,4,5-tetrahydro-1,4-benzothiazepine;

1,1-dioxo-3(S)-3-butyl-3-ethyl-5-(S)-5-phenyl-8-[N-((R)-α-carboxybenzyl) carbamoylmethoxy]-2,3,4,5-tetrahydro-1,4-benzothiazepine;

1,1-dioxo-3(R)-3-butyl-3-ethyl-5-(R)-5-phenyl-8-(N-{(R)-α-[N-(carboxymethyl)carbamoyl]benzyl}carbamoylmethoxy)-2,3,4,5-tetrahydro-1,4-benzothiazepine;

1,1-dioxo-3(S)-3-butyl-3-ethyl-5-(S)-5-phenyl-8-(N-{(R)-α-[N-(carboxymethyl)carbamoyl]benzyl}carbamoylmethoxy)-2,3,4,5-tetrahydro-1,4-benzothiazepine;

3,5-trans-1,1-dioxo-3-ethyl-3-butyl-5-phenyl-7-bromo-8-(N-{(R)-α-[N-(carboxymethyl) carbamoyl]benzyl}carbamoylmethoxy)-2,3,4,5-tetrahydro-1,4-benzothiazepine;

3,5-trans-1,1-dioxo-3-(S)-3-ethyl-3-butyl4-hydroxy-5-(S)-5-phenyl-7-bromo-8-(N-{(R)-α-[N-(carboxymethyl)carbamoyl]benzyl}carbamoylmethoxy)-2,3,4,5-tetrahydro-1,4-benzothiazepine 3,5-trans-1,1-dioxo-3-(R)-3-ethyl-3-butyl-4-hydroxy-5-(R)-5-phenyl-7-bromo-8-(N-{(R)-α-[N-(carboxymethyl)carbamoyl]benzyl}carbamoylmethoxy)-2,3,4,5-tetrahydro-1,4-benzothiazepine;

3,5-trans-1,1-dioxo-3-ethyl-3-butyl-5-phenyl-7-methylthio-8-(N-{(R)-α-[N-(carboxymethyl)carbamoyl]benzyl}carbamoylmethoxy)-2,3,4,5-tetrahydro-1,4-benzothiazepine;

3,5-trans-1,1-dioxo-3-ethyl-3-butyl-5-phenyl-7-methylthio-8-(N-{(R)-α-[N-(2-sulphoethyl)carbamoyl]hydroxybenzyl}carbamoylmethoxy)-2,3,4,5-tetrahydro-1,4-benzothiazepine ammonia salt;

1,1-dioxo-3-(S)-3-ethyl-3-butyl-5-(S)-5-phenyl-7-methylthio-8-(N-{R)-α-[N-(carboxymethyl) carbamoyl]benzyl}carbamoylmethoxy)-2,3,4,5-tetrahydro-1,4-benzothiazepine diethylamine salt; and 1,1-dioxo-3-(R)-3-ethyl-3-butyl-5-(R)-5-phenyl-7-methylthio-8-(N-{(R)-α-[N-(carboxymethyl) carbamoyl]benzyl}carbamoylmethoxy)-2,3,4,5-tetrahydro-1,4-benzothiazepine diethylamine salt;

or a pharmaceutically acceptable salt, solvate, solvate of such a salt or a prodrug thereof.

Additional suitable compounds of the invention are the IBAT inhibitors described in WO 03/022830. A particular compound of the invention is selected from any one of Example 1-4 of WO 03/022830, or a pharmaceutically acceptable salt, solvate, solvate of such a salt or a prodrug thereof, and the compounds of Examples 1-4 are incorporated herein by reference. Claims 1-8 of WO 03/022830 are also incorporated herein by reference. A particular compound of the invention selected from WO 03/022830 is selected from any one of:

1,1-dioxo-3-butyl-3-ethyl-4-hydroxy-5-phenyl-7-(N-{(R)-α-[N-(carboxymethyl) carbamoyl]benzyl}carbamoylmethylthio)-2,3,4,5-tetrahydrobenzothiepine 1,1-dioxo-3-butyl-3-ethyl4hydroxy-5-phenyl-7-(N-{(R)-α-[N-(2-sulphoethyl)carbamoyl]-4-hydroxybenzyl}carbamoylmethylthio)-2,3,4,5-tetrahydrobenzothiepine ammonia salt 1,1-dioxo-3-butyl-3-ethyl4-hydroxy-5-phenyl-7-{N-[α-(carboxy)-2-fluorobenzyl]carbamoylmethylthio}-2,3,4,5-tetrahydrobenzothiepine; and 1,1-dioxo-3-butyl-3-ethyl-4-hydroxy-5-phenyl-7-{N-[1-(carboxy)-1-(thien-2-yl)methyl]carbamoylmethylthio}-2,3,4,5-tetrahydrobenzothiepine or a pharmaceutically acceptable salt, solvate, solvate of such a salt or a prodrug thereof.

Additional suitable compounds of the invention are the IBAT inhibitors described in WO 03/022286. A particular compound of the invention is selected from any one of Example 1-39 of WO 03/022286, or a pharmaceutically acceptable salt, solvate, solvate of such a salt or a prodrug thereof, and the compounds of Examples 1-39 are incorporated herein by reference. Claims 1-10 of WO 03/022286 are also incorporated herein by reference. A particular compound of the invention selected from WO 03/022286 is selected from any one of:

1,1-dioxo-3,3-dibutyl-5-phenyl-7-methylthio-8-(N-{(R)-α-[N-((R)-1-carboxy-2-methylthio-ethyl) carbamoyl]-4-hydroxybenzyl}carbamoylmethoxy)-2,3,4,5-tetrahydro-1,2,5-benzothiadiazepine;

1,1-dioxo-3,3-dibutyl-5-phenyl-7-methylthio-8-(N-{(R)-α-[N-((S)-1-carboxy-2-(R)-hydroxypropyl) carbamoyl]-4-hydroxybenzyl}carbamoylmethoxy)-2,3,4,5-tetrahydro-1,2,5-benzothiadiazepine;

1,1-dioxo-3,3-dibutyl-5-phenyl-7-methylthio-8-(N-{(R)-α-[N-((S)-1-carboxy-2-methylpropyl)carbamoyl]hydroxybenzyl}carbamoylmethoxy)-2,3,4,5-tetrahydro-1,2,5-benzothiadiazepine;

1,1-dioxo-3,3-dibutyl-5-phenyl-7-methylthio-8-(N-{(R)-α-[N-((S)-1-carboxybutyl) carbamoyl]-4-hydroxybenzyl}carbamoylmethoxy)-2,3,4,5-tetrahydro-1,2,5-benzothiadiazepine;

1,1-dioxo-3,3-dibutyl-5-phenyl-7-methylthio-8-(N-{(R)-α-[N-((S)-1-carboxypropyl) carbamoyl] benzyl}carbamoylmethoxy)-2,3,4,5-tetrahydro-1,2,5-benzothiadiazepine;

1,1-dioxo-3,3-dibutyl-5-phenyl-7-methylthio-8-(N-{(R)-α-[N-((S)-1-carboxyethyl) carbamoyl] benzyl}carbamoylmethoxy)-2,3,4,5-tetrahydro-1,2,5-benzothiadiazepine;

1,1-dioxo-3,3-dibutyl-5-phenyl-7-methylthio-8-(N-{(R)-α-[N-((S)-1-carboxy-2-(R)-hydroxypropyl) carbamoyl] benzyl}carbamoylmethoxy)-2,3,4,5-tetrahydro-1,2,5-benzothiadiazepine;

1,1-dioxo-3,3-dibutyl-5-phenyl-7-methylthio-8-(N-{(R)-α-[N-(2-sulphoethyl)carbamoyl]-4-hydroxybenzyl}carbamoylmethoxy)-2,3,4,5-tetrahydro-1,2,5-benzothiadiazepine;

1,1-dioxo-3,3-dibutyl-5-phenyl-7-methylthio-8-(N-{(R)-α-[N-((S)-1-carboxyethyl)carbamoyl]-4-hydroxybenzyl}carbamoylmethoxy)-2,3,4,5-tetrahydro-1,2,5-benzothiadiazepine;

1,1-dioxo-3,3-dibutyl-5-phenyl-7-methylthio-8-(N-{(R)-α-[N-((R)-1-carboxy-2-methylthioethyl)carbamoyl] benzyl}carbamoylmethoxy)-2,3,4,5-tetrahydro-1,2,5-benzothiadiazepine;

1,1-dioxo-3,3-dibutyl-5-phenyl-7-methylthio-8-(N-{(R)-α-[N-{(S)-1-[N-((S)-2-hydroxy-1-carboxyethyl)carbamoyl] propyl}carbamoyl]benzyl}carbamoylmethoxy)-2,3,4,5-tetrahydro-1,2,5-benzothiadiazepine; and 1,1-dioxo-3,3-dibutyl-5-phenyl-7-methylthio-8-(N-{(R)-α-[N-((S)-1-carboxy-2-methylpropyl)carbamoyl] benzyl}carbamoylmethoxy)-2,3,4,5-tetrahydro-1,2,5-benzothiadiazepine;

or a pharmaceutically acceptable salt, solvate, solvate of such a salt or a prodrug thereof.

A further particular compound of the invention selected from WO 03/022286 is selected from any one of:

1,1-dioxo-3,3-dibutyl-5-phenyl-7-methylthio-8-(N-{(R)-α-[N-((S)-1-carboxypropyl)carbamoyl]-4-hydroxybenzyl}carbamoylmethoxy)-2,3,4,5-tetrahydro-1,2,5-benzothiadiazepine; and 1,1-dioxo-3,3-dibutyl-5-phenyl-7-methylthio-8-[N-((R)-α-carboxy-4-hydroxybenzyl)carbamoylmethoxy]-2,3,4,5-tetrahydro-1,2,5-benzothiadiazepine;

or a pharmaceutically acceptable salt, solvate, solvate of such a salt or a prodrug thereof.

Further suitable IBAT inhibitors are those having the structure:

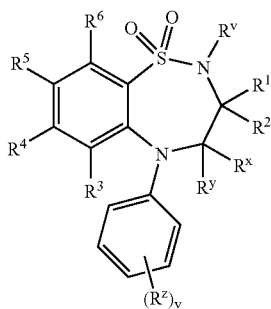

(I)

wherein:

$R^v$ is selected from hydrogen or $C_{1-6}$alkyl;

One of $R^1$ and $R^2$ are selected from hydrogen or $C_{1-6}$alkyl and the other is selected from $C_{1-6}$alkyl;

$R^x$ and $R^y$ are independently selected from hydrogen, hydroxy, amino, mercapto, $C_{1-6}$alkyl, $C_{1-6}$alkoxy, N-($C_{1-6}$alkyl)amino, N,N-($C_1$alkyl)$_2$amino, $C_{1-6}$alkyl$_2$(O)$_a$ wherein a is 0 to 2;

$R^z$ is selected from halo, nitro, cyano, hydroxy, amino, carboxy, carbamoyl, mercapto, sulphamoyl, $C_{1-6}$alkyl, $C_{2-6}$alkenyl, $C_{2-6}$alkynyl, $C_{1-6}$alkoxy, $C_{1-6}$alkanoyl, $C_{1-6}$alkanoyloxy, N-($C_{1-6}$alkyl)amino, N,N-($C_{1-6}$alkyl)$_2$amino, $C_{1-6}$alkanoylamino, N-($C_{1-6}$alkyl)carbamoyl, N,N-($C_{1-6}$alkyl)$_2$carbamoyl, $C_{1-6}$alkylS(O)$_a$ wherein a is 0 to 2, $C_{1-6}$alkoxycarbonyl, N-($C_{1-6}$alkyl)sulphamoyl and N,N-($C_{1-6}$alkyl)$_2$sulphamoyl;

v is 0-5;

one of $R^4$ and $R^5$ is a group of formula (A):

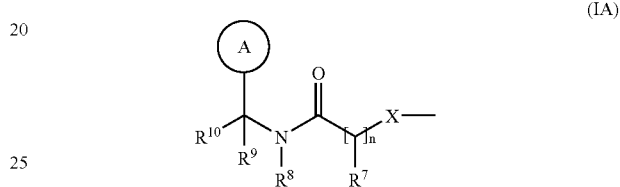

(IA)

$R^3$ and $R^6$ and the other of $R^4$ and $R^5$ are independently selected from hydrogen, halo, nitro, cyano, hydroxy, amino, carboxy, carbamoyl, mercapto, sulphamoyl, $C_{1-6}$alkyl, $C_{2-6}$alkenyl, $C_{2-6}$alkynyl, $C_{1-6}$alkoxy, $C_{1-6}$alkanoyl, $C_{1-6}$alkanoyloxy, N-($C_{1-6}$alkyl)amino, N,N-($C_{1-6}$alkyl)$_2$amino, $C_{1-6}$alkanoylamino, N-($C_{1-6}$alkyl)carbamoyl, N,N-($C_{1-6}$alkyl)$_2$carbamoyl, $C_{1-6}$alkylS(O)$_a$ wherein a is 0 to 2, $C_{1-6}$alkoxycarbonyl, N-($C_{1-6}$alkyl)sulphamoyl and N,N-($C_{1-6}$alkyl)$_2$sulphamoyl; wherein $R^3$ and $R^6$ and the other of $R^4$ and $R^5$ may be optionally substituted on carbon by one or more $R^{17}$;

X is —O—, —N($R^a$)—, —S(O)$_b$— or —CH($R^a$)—; wherein $R^a$ is hydrogen or $C_{1-6}$alkyl and b is 0-2;

Ring A is aryl or heteroaryl; wherein Ring A is optionally substituted on carbon by one or more substituents selected from $R^{18}$;

$R^7$ is hydrogen, $C_{1-6}$alkyl, carbocyclyl or heterocyclyl; wherein $R^7$ is optionally substituted on carbon by one or more substituents selected from $R^{19}$; and wherein if said heterocyclyl contains an —NH— group, that nitrogen may be optionally substituted by a group selected from $R^{20}$;

$R^8$ is hydrogen or $C_{1-4}$alkyl;

$R^9$ is hydrogen or $C_{1-6}$ alkyl;

$R^{10}$ is hydrogen, halo, nitro, cyano, hydroxy, amino, carbamoyl, mercapto, sulphamoyl, hydroxyaminocarbonyl, $C_{1-10}$alkyl, $C_{2-10}$alkenyl, $C_{2-10}$alkyl, $C_{1-10}$alkoxy, $C_{1-10}$alkanoyl, $C_{1-10}$alkanoyloxy, N-($C_{1-10}$alkyl)amino, N,N-($C_{1-10}$alkyl)$_2$amino, N,N,N-($C_{1-10}$alkyl)$_3$ammonio, $C_{1-10}$alkanoylamino, N-($C_{1-10}$alkyl)carbamoyl, N,N-($C_{1-10}$alkyl)$_2$ carbamoyl, $C_{1-10}$alkylS(O)$_a$ wherein a is 0 to 2, N-($C_{1-10}$alkyl)sulphamoyl, N,N-($C_{1-10}$alkyl)$_2$sulphamoyl, N-($C_{1-10}$alkyl)sulphamoylamino, N,N-($C_{1-10}$alkyl)$_2$sulphamoylamino, $C_{1-10}$alkoxycarbonylamino, carbocyclyl, carbocyclyl$C_{1-10}$ alkyl, heterocyclyl, heterocyclyl$C_{1-10}$alkyl, carbocyclyl-($C_{1-10}$alkylene)$_p$-$R^{21}$-($C_{1-10}$alkylene)$_q$- or heterocyclyl-($C_{1-10}$alkylene)$_r$-$R^{22}$-($C_{1-10}$alkylene)$_s$-; wherein $R^{10}$ is optionally substituted on carbon by one or more substituents selected from $R^{23}$; and wherein if said heterocyclyl contains an —NH— group, that nitrogen may be optionally substituted by a group selected from $R^{24}$; or $R^{10}$ is a group of formula (IB):

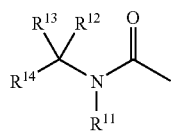

wherein:

$R^{11}$ is hydrogen or $C_{1-6}$alkyl;

$R^{12}$ and $R^{13}$ are independently selected from hydrogen, halo, carbamoyl, sulphamoyl, $C_{1-10}$alkyl, $C_{2-10}$alkenyl, $C_{2-10}$alkynyl, $C_{1-10}$alkanoyl, N-($C_{1-10}$alkyl)carbamoyl, N,N-($C_{-1-10}$alkyl)$_2$carbamoyl, $C_{1-10}$alkylS(O)$_a$ wherein a is 0 to 2, N-($C_{1-10}$alkyl)sulphamoyl, N,N-($C_{1-10}$alkyl)$_2$sulphamoyl, N-($C_{1-10}$alkyl)sulphamoylamino, N,N-($C_{1-10}$alkyl)$_2$sulphamoylamino, carbocyclyl or heterocyclyl; wherein $R^{12}$ and $R^{13}$ may be independently optionally substituted on carbon by one or more substituents selected from $R^{25}$; and wherein if said heterocyclyl contains an —NH— group, that nitrogen may be optionally substituted by a group selected from $R^{26}$;

$R^{14}$ is selected from hydrogen, halo, carbamoyl, sulphamoyl, hydroxyaminocarbonyl, $C_{1-10}$alkyl, $C_{2-10}$alkenyl, $C_{2-10}$alkyl, $C_{1-10}$alkynyl, N-($C_{1-10}$alkyl)carbamoyl, N,N-($C_{1-10}$alkyl)$_2$carbamoyl, $C_{1-10}$alkylS(O)$_a$ wherein a is 0 to 2, N-($C_{1-10}$alkyl)sulphamoyl, N,N-($C_{1-10}$alkyl)$_2$sulphamoyl, N-($C_{1-10}$alkyl)sulphamoylamino, N,N-($C_{1-10}$alklyl)$_2$sulphamoylamino, carbocyclyl, carbocyclyl$_{1-10}$alkyl, heterocyclyl, heterocyclylC$_{1-10}$alkyl, carbocyclyl-($C_{1-10}$alkylene)$_p$-$R^{27}$-($C_{1-10}$alkylene)$_q$- or heterocyclyl-($C_{1-10}$alkylene)$_r$-$R^{28}$-($C_{1-10}$ alkylene)$_s$-; wherein $R^{14}$ may be optionally substituted on carbon by one or more substituents selected from $R^{29}$; and wherein if said heterocyclyl contains an —NH— group, that nitrogen may be optionally substituted by a group selected from $R^{30}$; or $R^{14}$ is a group of formula (IC):

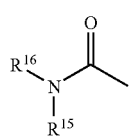

$R^{15}$ is hydrogen or $C_{1-6}$alkyl; and $R^{16}$ is hydrogen or $C_{1-6}$alkyl; wherein $R^{16}$ may be optionally substituted on carbon by one or more groups selected from $R^{31}$; or $R^{15}$ and $R^{16}$ together with the nitrogen to which they are attached form a heterocyclyl; wherein said heterocyclyl may be optionally substituted on carbon by one or more $R^{37}$; and wherein if said heterocyclyl contains an —NH— group, that nitrogen may be optionally substituted by a group selected from $R^{38}$;

n is 1-3; wherein the values of $R^7$ may be the same or different;

$R^{17}$, $R^{18}$, $R^{19}$, $R^{23}$, $R^{25}$, $R^{29}$, $R^{31}$ and $R^{37}$ are independently selected from halo, nitro, cyano, hydroxy, amino, carbamoyl, mercapto, sulphamoyl, hydroxyaminocarbonyl, $C_{1-10}$alkyl, $C_{2-10}$alkenyl, $C_{2-10}$alkynyl, $C_{1-10}$alkoxy, $C_{1-10}$alkanoyl, $C_{1-10}$alkanoyloxy, N-($C_{1-10}$alkyl)amino, N,N-($C_{1-10}$alkyl)$_2$amino, N,N,N-($C_{1-10}$alkyl)$_3$ammonio, $C_{1-10}$alkanoylamino, N-($C_{1-10}$alkyl)carbamoyl, N,N-($C_{1-10}$alkyl)$_2$carbamoyl, $C_{1-10}$alkylS(O)$_a$ wherein a is 0 to 2, N-($C_{1-10}$alkyl)sulphamoyl, N,N-($C_{1-10}$alkyl)$_2$sulphamoyl, N-($C_{1-10}$alkyl)sulphamoylamino, N,N-($C_{1-10}$alkyl)$_2$sulphamoylamino, $C_{1-10}$alkoxycarbonylamino, carbocyclyl, carbocyclylC$_{1-10}$alkyl, heterocyclyl, heterocyclylC$_{1-10}$alkyl, carbocyclyl-($C_{1-10}$ alkylene)$_p$-$R^{32}$-($C_{1-10}$alkylene)$_q$- or heterocyclyl-($C_{1-10}$ alkylene)$_r$-$R^{33}$-($C_{1-10}$alkylene)$_s$-; wherein $R^{17}$, $R^{18}$, $R^{19}$, $R^{23}$, $R^{25}$, $R^{29}$, $R^{31}$ and $R^{37}$ may be independently optionally substituted on carbon by one or more $R^{34}$; and wherein if said heterocyclyl contains an —NH— group, that nitrogen may be optionally substituted by a group selected from $R^{35}$;

$R^{21}$, $R^{22}$, $R^{27}$, $R^{28}$, $R^{32}$ or $R^{33}$ are independently selected from —O—, —NR$^{36}$—, —S(O)$_x$—, —NR$^{36}$C(O)NR$^{36}$—, —NR$^{36}$C(S)NR$^{36}$—, —OC(O)N=C—, —NR$^{36}$C(O)— or —C(O)NR$^{36}$—; wherein $R^{36}$ is selected from hydrogen or $C_{1-6}$alkyl, and x is 0-2;

p, q, r and s are independently selected from 0-2;

$R^{34}$ is selected from halo, hydroxy, cyano, carbamoyl, ureido, amino, nitro, carbamoyl, mercapto, sulphamoyl, trifluoromethyl, trifluoromethoxy, methyl, ethyl, methoxy, ethoxy, vinyl, allyl, ethynyl, formyl, acetyl, formamido, acetylamino, acetoxy, methylamino, dimethylamino, N-methylcarbamoyl, N,N-dimethylcarbamoyl, methylthio, methylsulphinyl, mesyl, N-methylsulphamoyl, N,N-dimethylsulphamoyl, N-methylsulphamoylamino and N,N-dimethylsulphamoylamino;

$R^{20}$, $R^{24}$, $R^{26}$, $R^{30}$, $R^{35}$ and $R^{38}$ are independently selected from $C_{1-6}$alkyl, $C_{1-6}$alkanoyl, $C_{1-6}$alkylsulphonyl, $C_{1-6}$alkoxycarbonyl, carbamoyl, N-($C_{1-6}$alkyl)carbamoyl, N,N-($C_{1-6}$alkyl)carbamoyl, benzyl, benzyloxycarbonyl, benzoyl and phenylsulphonyl; or a pharmaceutically acceptable salt, solvate, solvate of such a salt or a prodrug thereof.

Suitable IBAT inhibitors having the above structure are selected from any one of:

1,1-Dioxo-3,3-dibutyl-5-phenyl-7-methylthio-8-(N-{(R)-α-[N-(2-(S)-3-(R)-4-(R)-5-(R)-2,3,4,5,6-pentahydroxyhexyl)carbamoyl]benzyl}carbamoylmethoxy)-2,3,4,5-tetrahydro-1,2,5-benzothiadiazepine;

1,1-Dioxo-3,3-dibutyl-5-phenyl-7-methylthio-8-(N-{(R)-α-[N-(2-(S)-3-(R)-4)-5-(R)-2,3,4,5 ,6-pentahydroxyhexyl)carbamoyl]-4-hydroxybenzyl}carbamoylmethoxy)-2,3,4,5-tetrahydro-1,2,5-benzothiadiazepine;

1,1-Dioxo-3,3-dibutyl-5-phenyl-7-methylthio-8-[N-((R/S)-α-{N-[1-(R)-2-(S)-1-hydroxy-1-(3,4-dihydroxyphenyl)prop-2-yl]carbamoyl}benzyl)carbamoylmethoxy]-2,3,4,5-tetrahydro-1,2,5-benzothiadiazepine (both enantiomers);

1,1-Dioxo-3,3-dibutyl-5-phenyl-7-methylthio-8-{N-[(R)-α-(N-{2-(S)-[N-(carbamoylmethyl) carbamoyl]pyrrolidin-1-ylcarbonylmethyl}carbamoyl)benzyl]carbamoylmethoxy}-2,3,4,5-tetrahydro-1,2,5-benzothiadiazepine;

1,1-Dioxo-3,3-dibutyl-5-phenyl-7-methylthio-8-[N-((R)-α-{N-[2-(3,4,5-trihydroxyphenyl)ethyl]carbamoyl}benzyl)carbamoylmethoxy]-2,3,4,5-tetrahydro-1,2,5-benzothiadiazepine; or 1,1-Dioxo-3,3-dibutyl-5-phenyl-7-methylthio-8-(N-{(R)-α-[N-(2-(R)-3-(S)4-(S)-5-(R)-3,4,5,6-tetrahydroxytetrahydropyran-2-ylmethyl)carbamoyl]benzyl}carbamoylmethoxy)-2,3,4,5-tetrahydro-1,2,5-benzothiadiazepine;

or a pharmaceutically acceptable salt, solvate, solvate of such a salt or a prodrug thereof.

Further suitable IBAT inhibitors are those having the structure:

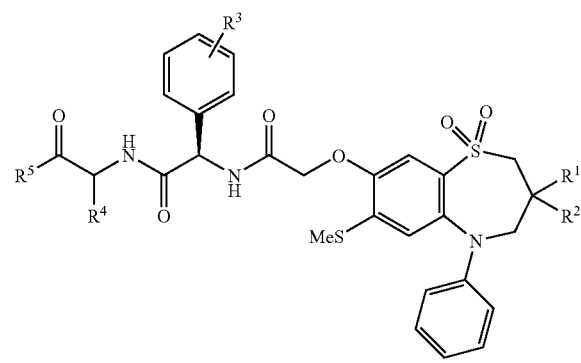

wherein:

R$^1$ and R$^2$ are independently selected from C$_{1-4}$alkyl;

R$^3$ is hydrogen, hydroxy or halo;

R$^4$ is C$_{1-4}$alkyl optionally substituted by hydroxy, methoxy and methylS(O)a wherein a is 0-2

R$^5$ is hydroxy or HOC(O)CH(R$^6$)NH—;

R$^6$ is selected from hydrogen and C$_{1-3}$alkyl optionally substituted by hydroxy, methoxy and methylS(O)$_a$ wherein a is 0-2;

or a pharmaceutically acceptable salt, solvate, solvate of such a salt or a prodrug thereof; with the proviso that when R$^1$ and R$^2$ are both butyl, R$^5$ is hydroxy and R$^4$ is methylthiomethyl, methylsulphinylmethyl, 2-methylthioethyl, hydroxymethyl, methoxymethyl; R$^3$ is not hydrogen; and with the proviso that when R$^1$ and R$^2$ are both butyl, R$^5$ is HOC(O)CH(R$^6$)NH—, R$^6$ is hydroxymethyl and R$^4$ is hydroxymethyl; R$^3$ is not hydrogen.

Suitable IBAT inhibitors having the above structure are selected from any one of:

1,1-dioxo-3,3-dibutyl-5-phenyl-7-methylthio-8-(N-{(R)-α-[N'-((S)-1-carboxyethyl) carbamoyl]benzyl}carbamoylmethoxy)-2,3,4,5-tetrahydro-1,5-benzothiazepine;

1,1-dioxo-3,3-dibutyl-5-phenyl-7-methylthio-8-(N-{(R)-α-[N'-((S)-1-carboxypropyl) carbamoyl]benzyl}carbamoylmethoxy)-2,3,4,5-tetrahydro-1,5-benzothiazepine;

1,1-dioxo-3,3-dibutyl-5-phenyl-7-methylthio-8-(N-{(R)-α-[N'-((S)-1-carboxybutyl) carbamoyl]benzyl}carbamoylmethoxy)-2,3,4,5-tetrahydro-1,5-benzothiazepine;

1,1-dioxo-3,3-dibutyl-5-phenyl-7-methylthio-8-(N-{(R)-α-[N'-((S)-1-carboxy-2-methylpropyl)carbamoyl]benzyl}carbamoylmethoxy)-2,3,4,5-tetrahydro-1,5-benzothiazepine;

1,1-dioxo-3,3-dibutyl-5-phenyl-7-methylthio-8-(N-{(R)-α-[N'-((S)-1-carboxy-2-methylbutyl)carbamoyl]benzyl}carbamoylmethoxy)-2,3,4,5-tetrahydro-1,5-benzothiazepine;

1,1-dioxo-3,3-dibutyl-5-phenyl-7-methylthio-8-(N-{(R)-α-[N'-((S)-1-carboxy-3-methylbutyl)carbamoyl]benzyl}carbamoylmethoxy)-2,3,4,5-tetrahydro-1,5-benzothiazepine;

1,1-dioxo-3,3-dibutyl-5-phenyl-7-methylthio-8-(N-{(R)-α-[N'-((S)-1-carboxy-2-hydroxypropyl)carbamoyl]benzyl}carbamoylmethoxy)-2,3,4,5-tetrahydro-1,5-benzothiazepine;

1,1-dioxo-3,3-dibutyl-5-phenyl-7-methylthio-8-(N-{(R)-α-[N-((S)-1-carboxy-2-mesylethyl)carbamoyl]benzyl}carbamoylmethoxy)-2,3,4,5-tetrahydro-1,5-benzothiazepine;

1,1-dioxo-3,3-dibutyl-5-phenyl-7-methylthio-8-(N-{(R)-α-[N'-((S)-1-carboxy-3-methylsulphonylpropyl)carbamoyl]benzyl}carbamoylmethoxy)-2,3,4,5-tetrahydro-1,5-benzothiazepine;

1,1-dioxo-3,3-dibutyl-5-phenyl-7-methylthio-8-(N-{(R)-α-[N'-((S)-1-carboxy-3-mesylpropyl)carbamoyl]benzyl}carbamoylmethoxy)-2,3,4,5-tetrahydro-1,5-benzothiazepine;

1,1-dioxo-3,3-dibutyl-5-phenyl-7-methylthio-8-(N-{(R)-α-[N'-((S)-1-carboxyethyl) carbamoyl]-4-hydroxybenzyl}carbamoylmethoxy)-2,3,4,5-tetrahydro-1,5-benzothiazepine;

1,1-dioxo-3,3-dibutyl-5-phenyl-7-methylthio-8-(N-{(R)-α-[N'-((S)-1-carboxypropyl) carbamoyl]-4-hydroxybenzyl}carbamoylmethoxy)-2,3,4,5-tetrahydro-1,5-benzothiazepine;

1,1-dioxo-3,3-dibutyl-5-phenyl-7-methylthio-8-(N-{(R)-α-[N'-((S)-1-carboxybutyl) arbamoyl]-4-hydroxybenzyl}carbamoylmethoxy)-2,3,4,5-tetrahydro-1,5-benzothiazepine;

1,1-dioxo-3,3-dibutyl-5-phenyl-7-methylthio-8-(N-{(R)-α-[N'-((S)-1-carboxy-2-methylpropyl)carbamoyl] hydroxybenzyl}carbamoylmethoxy)-2,3,4,5-tetrahydro-1,5-benzothiazepine;

1,1-dioxo-3 ,3-dibutyl-5-phenyl-7-methylthio-8-(N-{(R)-α-[N'-((S)-1-carboxy-2-methylbutyl)carbamoyl]-4-hydroxybenzyl}carbamoylmethoxy)-2,3,4,5-tetrahydro-1,5-benzothiazepine;

1,1-dioxo-3,3-dibutyl-5-phenyl-7-methylthio-8-(N-{(R)-α-[N'-((S)-1-carboxy-3-methylbutyl)carbamoyl]-4-hydroxybenzyl}carbamoylmethoxy)-2,3,4,5-tetrahydro-1,5-benzothiazepine;

1,1-dioxo-3,3-dibutyl-5-phenyl-7-methylthio-8-(N-{(R)-α-[N'-((S)-1-carboxy-2-hydroxyethyl)carbamoyl]-4-hydroxybenzyl}carbamoylmethoxy)-2,3,4,5-tetrahydro-1,5-benzothiazepine;

1,1-dioxo-3,3-dibutyl-5-phenyl-7-methylthio-8-(N-{(R)-α-[N'-((S)-1-carboxy-2-hydroxypropyl)carbamoyl]-4hydroxybenzyl}carbamoylmethoxy)-2,3,4,5-tetrahydro-1,5-benzothiazepine;

1,1-dioxo-3,3-dibutyl-5-phenyl-7-methylthio-8-(N-{(R)-α-[N'-((S)-1-carboxy-2-methylthioethyl)carbamoyl]-4-hydroxybenzyl}carbamoylmethoxy)-2,3,4,5-tetrahydro-1,5-benzothiazepine;

1,1-dioxo-3,3-dibutyl-5-phenyl-7-methylthio-8-(N-{(R)-α-[N'-((S)-1-carboxy-2-methylsulphinylethyl)carbamoyl]-4-hydroxybenzyl}carbamoylmethoxy)-2,3,4,5-tetrahydro-1,5-benzothiazepine;

1,1-dioxo-3,3-dibutyl-5-phenyl-7-methylthio-8-(N-{(R)-α-[N'-((S)-1-carboxy-2-mesylethyl)carbamoyl]-4-hydroxybenzyl}carbamoylmethoxy)-2,3,4,5-tetrahydro-1,5-benzothiazepine;

1,1-dioxo-3,3-dibutyl-5-phenyl-7-methylthio-8-(N-{(R)-α-[N'-((S)-1-carboxy-2-methoxyethyl)carbamoyl]-4-hydroxybenzyl}carbamoylmethoxy)-2,3,4,5-tetrahydro-1,5-benzothiazepine;

1,1-dioxo-3,3-dibutyl-5-phenyl-7-methylthio-8-(N-{(R)-α-[N'-((S)-1-carboxy-3-methylthiopropyl)carbamoyl]-4-hydroxybenzyl}carbamoylmethoxy)-2,3,4,5-tetrahydro-1,5-benzothiazepine;

1,1-dioxo-3,3-dibutyl-5-phenyl-7-methylthio-8-(N-{(R)-α-[N'-((S)-1-carboxy-3-methylsulphonylpropyl)carbamoyl]-4-hydroxybenzyl}carbamoylmethoxy)-2,3,4,5-tetrahydro-1,5-benzothiazepine; or 1,1-dioxo-3,3-dibutyl-5-phenyl-7-methylthio-8-(N-{(R)-α-[N'-((S)-1-carboxy-3-mesylpropyl)carbamoyl]-4-hydroxybenzyl}carbamoylmethoxy)-2,3,4,5-tetrahydro-1,5-benzothiazepine;

or a pharmaceutically acceptable salt, solvate, solvate of such a salt or a prodrug thereof.

Additional suitable IBAT inhibitors having the above structure are selected from:

1,1-dioxo-3,3-dibutyl-5-phenyl-7-methylthio-8-(N-{(R)-α-[N'-((S)-1-carboxypropyl)carbamoyl]-4-hydroxybenzyl}carbamoylmethoxy)-2,3,4,5-tetrahydro-1,5-benzothiazepine; or 1,1-dioxo-3,3-dibutyl-5-phenyl-7-methylthio-8-(N-{(R)-α-[N'-((S)-1-carboxyethyl) carbamoyl]benzyl}carbamoylmethoxy)-2,3,4,5-tetrahydro-1,5-benzothiazepine.

Further suitable IBAT inhibitors are those having the structure:

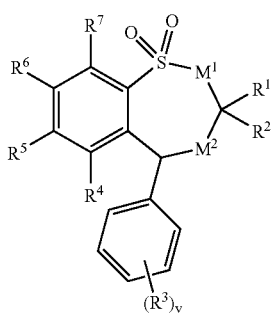

(I)

wherein $M^1$ is —CH$_2$— or —NR$^{21}$—;

$M^2$ is —CR$^{22}$R$^{23}$— or —NR$^{24}$; provided that if $M^1$ is —NR$^{21}$—, $M^2$ is —CR$^{22}$R$^{23}$—;

One of $R^1$ and $R^2$ are selected from hydrogen, $C_{1-6}$ alkyl or $C_{2-6}$alkenyl and the other is selected from $C_{1-6}$alkyl or $C_{2-6}$alkenyl;

$R^3$ is selected from halo, nitro, cyano, hydroxy, amino, carboxy, carbamoyl, mercapto, sulphamoyl, $C_{1-6}$alkyl, $C_{2-6}$alkenyl, $C_{2-6}$alkynyl, $C_{1-6}$alkoxy, $C_{1-6}$alkanoyl, $C_{1-6}$alkanoyloxy, N-($C_{1-6}$alkyl)amino, N,N-($C_{1-6}$alkyl)$_2$amino, $C_{1-6}$alkanoylamino, N-($C_{1-6}$alkyl)carbamoyl, N,N-($C_{1-6}$alkyl)$_2$carbamoyl, $C_{1-6}$alkylS(O)$_a$ wherein a is 0 to 2, $C_{1-6}$alkoxycarbonyl, N-($C_{1-6}$alkyl)sulphamoyl and N,N-($C_{1-6}$alkyl)$_2$sulphamoyl;

v is 0-5;

one of $R^5$ and $R^6$ is a group of formula (IA):

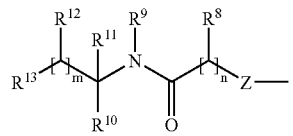

(IA)

$R^4$ and $R^7$ and the other of $R^5$ and $R^6$ are independently selected from hydrogen, halo, nitro, cyano, hydroxy, amino, carboxy, carbamoyl, mercapto, sulphamoyl, $C_{1-4}$alkyl, $C_{2-4}$alkenyl, $C_{2-4}$alkynyl, $C_{1-4}$alkoxy, $C_{1-4}$alkanoyl, $C_{1-4}$alkanoyloxy, N-($C_{1-4}$allyl)amino, N,N-($C_{1-4}$-alkyl)$_2$amino, $C_{1-4}$alkanoylamino, N-($C_{1-4}$alkyl)carbamoyl, N,N-($C_{1-4}$alkyl)$_2$carbamoyl, $C_{1-4}$alkylS(O)$_a$ wherein a is 0 to 2, $C_{1-4}$alkoxycarbonyl, N-($C_{1-4}$alkyl)sulphamoyl and N,N-($C_{1-4}$ alkyl)$_2$sulphamoyl; wherein $R^4$ and $R^7$ and the other of $R^5$ and $R^6$ may be optionally substituted on carbon by one or more $R^{25}$;

Z is —O—, —N($R^a$)—, —S(O)$_b$— or —CH($R^a$)—; wherein $R^a$ is hydrogen or $C_{1-6}$alkyl and b is 0-2;

$R^8$ is hydrogen, $C_{1-4}$-alkyl, carbocyclyl or heterocyclyl; wherein $R^8$ may be optionally substituted on carbon by one or more substituents selected from $R^{26}$; and wherein if said heterocyclyl contains an —NH— group, that nitrogen may be optionally substituted by a group selected from $R^{27}$;

$R^9$ is hydrogen or $C_{1-4}$alkyl;

$R^{10}$ and $R^{11}$ are independently selected from hydrogen, $C_{1-4}$alkyl, carbocyclyl or heterocyclyl; or $R^{10}$ and $R^{11}$ together form $C_{2-6}$alkylene; wherein $R^{10}$ and $R^{11}$ or $R^{10}$ and $R^{11}$ together may be independently optionally substituted on carbon by one or more substituents selected from $R^{28}$; and wherein if said heterocyclyl contains an —NH— moiety, that nitrogen may be optionally substituted by one or more $R^{29}$;

$R^{12}$ is hydrogen, $C_{1-4}$alkyl, carbocyclyl or heterocyclyl; wherein $R^{12}$ may be optionally substituted on carbon by one or more substituents selected from $R^{30}$; and wherein if said heterocyclyl contains an —NH— moiety, that nitrogen may be optionally substituted by one or more $R^{31}$;

$R^{13}$ is hydrogen, halo, nitro, cyano, hydroxy, amino, carbamoyl, mercapto, sulphamoyl, hydroxyaminocarbonyl, $C_{1-10}$allyl, $C_{2-10}$alkenyl, $C_{2-10}$alkynyl, $C_{1-10}$alkoxy, $C_{1-10}$alkoxycarbonyl, $C_{1-10}$alkanoyl, $C_{1-10}$alkanoyloxy, N-($C_{1-10}$alkyl)amino, N,N-($C_{1-10}$alkyl)$_2$amino, N,N,N-($C_{1-10}$ alkyl)$_3$ammonio, $C_{1-10}$alkanoylamino, N-($C_{1-10}$alkyl)carbamoyl, N,N-($C_{1-10}$alkyl)$_2$carbamoyl, $C_{1-10}$alkylS(O)$_a$ wherein a is 0 to 2, N-($C_{1-10}$alkyl)sulphamoyl, N,N-($C_{1-10}$alkyl)$_2$sulphamoyl, N-($C_{1-10}$alkyl)sulphamoylamino, N,N-($C_{1-10}$alkyl)$_2$sulphamoylamino, $C_{1-10}$alkoxycarbonylamino, carbocyclyl, carbocyclyl$C_{1-10}$allyl, heterocyclic group, heterocyclyl$C_{1-10}$allyl, carbocyclyl-($C_{1-10}$alkylene)$_e$-R$^{32}$-($C_{1-10}$alkylene)$_f$- or heterocyclyl-($C_{1-10}$alkylene)$_g$-R$^{33}$-($C_{1-10}$alkylene)$_h$-; wherein $R^{13}$ may be optionally substituted on carbon by one or more substituents selected from $R^{36}$; and wherein if said heterocyclyl contains an —NH— group, that nitrogen may be optionally substituted by a group selected from $R^{37}$; or $R^{13}$ is a group of formula (IB):

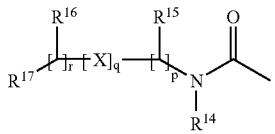

(IB)

wherein:

X is —N(R$^{38}$)—, —N(R$^{38}$)C(O)—, —O—, and —S(O)$_a$—; wherein a is 0-2 and R$^{38}$ is hydrogen or C$_{1-4}$alkyl;

R$^{14}$ is hydrogen or C$_{1-4}$alkyl;

R$^{15}$ and R$^{16}$ are independently selected from hydrogen, halo, nitro, cyano, hydroxy, amino, carbamoyl, mercapto, sulphamoyl, C$_{1-6}$alkyl, C$_{2-6}$alkenyl, C$_{2-6}$alkynyl, C$_{1-6}$alkoxy, C$_{1-6}$alkanoyl, C$_{1-6}$alkanoyloxy, N-(C$_{1-6}$alkyl)amino, N,N-(C$_{1-6}$alkyl)$_2$amino, C$_{1-6}$alkanoylamino, N-(C$_{1-6}$alkyl)carbamoyl, N,N-(C$_{1-6}$alkyl)$_2$carbamoyl, C$_{1-6}$alkylS(O)$_a$ wherein a is 0 to 2, C$_{1-6}$alkoxycarbonyl, N-(C$_{1-6}$alkyl)sulphamoyl, N,N-(C$_{1-6}$alkyl)$_2$sulphamoyl, carbocyclyl or heterocyclic group; wherein R$^{15}$ and R$^{16}$ may be independently optionally substituted on carbon by one or more substituents selected from R$^{41}$; and wherein if said heterocyclyl contains an —NH— group, that nitrogen may be optionally substituted by a group selected from R$^{42}$;

R$^{17}$ is selected from hydrogen, halo, nitro, cyano, hydroxy, amino, carbamoyl, mercapto, sulphamoyl, hydroxyaminocarbonyl, C$_{1-10}$allyl, C$_{2-10}$alkenyl, C$_{2-10}$alkynyl, C$_{1-10}$alkoxy, C$_{1-10}$alkanoyl, C$_{1-10}$alkanoyloxy, N-(C$_{1-10}$alkyl)amino, N,N-(C$_{1-10}$alkyl)$_2$amino, C$_{1-10}$alkanoylamino, N-(C$_{1-10}$alkyl)carbamoyl, C$_{1-10}$alkoxycarbonyl, N,N-(C$_{1-10}$alkyl)$_2$carbamoyl, C$_{1-10}$alkylS(O)$_a$ wherein a is 0 to 2, N-(C$_{1-10}$alkyl)sulphamoyl, N,N-(C$_{1-10}$alkyl)$_2$sulphamoyl, N-(C$_{1-10}$ alkyl)sulphamoylamino, N,N-(C$_{1-10}$alkyl)$_2$ sulphamoylamino, carbocyclyl, carbocyclylC$_{1-10}$alkyl, heterocyclic group, heterocyclylC$_{1-10}$alkyl, carbocyclyl-(C$_{1-10}$alkylene)$_e$-R$^{43}$-(C$_{1-10}$alkylene)$_f$- or heterocyclyl-(C$_{1-10}$alkylene)$_g$-R$^{44}$-(C$_{1-10}$alkylene)$_h$-; wherein R$^{17}$ may be optionally substituted on carbon by one or more substituents selected from R$^{47}$; and wherein if said heterocyclyl contains an —NH— group, that nitrogen may be optionally substituted by a group selected from R$^{48}$; or R$^{17}$ is a group of formula (IC):

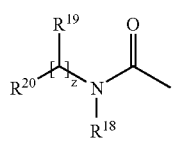

(IC)

wherein:

R$^{18}$ is hydrogen or C$_{1-4}$alkyl;

R$^{19}$ is selected from hydrogen, halo, nitro, cyano, hydroxy, amino, carbamoyl, mercapto, sulphamoyl, C$_{1-6}$alkyl, C$_{2-6}$alkenyl, C$_{2-6}$alkynyl, C$_{1-6}$alkoxy, C$_{1-6}$alkanoyl, C$_{1-6}$alkanoyloxy, N-(C$_{1-6}$alkyl)amino, N,N-(C$_{1-6}$alkyl)$_2$amino, C$_{1-6}$alkanoylamino, N-(C$_{1-6}$alkyl)carbamoyl, N,N-(C$_{1-6}$alkyl)$_2$carbamoyl, C$_{1-6}$alkylS(O)$_a$ wherein a is 0 to 2, C$_{1-6}$alkoxycarbonyl, N-(C$_{1-6}$alkyl)sulphamoyl, N,N-(C$_{1-6}$alkyl)$_2$sulphamoyl, carbocyclyl or heterocyclic group; where R$^{19}$ may be independently optionally substituted on carbon by one or more substituents selected from R$^{51}$; and wherein if said heterocyclyl contains an —NH— group, that nitrogen may be optionally substituted by a group selected from R$^{52}$;

R$^{20}$ is selected from halo, nitro, cyano, hydroxy, amino, carbamoyl, mercapto, sulphamoyl, hydroxyaminocarbonyl, C$_{1-10}$alkyl, C$_{2-10}$alkenyl, C$_{2-10}$alkynyl, C$_{1-10}$alkoxy, C$_{1-10}$alkoxycarbonyl, C$_{1-10}$alkanoyl, C$_{1-10}$alkanoyloxy, N-(C$_{1-10}$alkyl)amino, N,N-(C$_{1-10}$alkyl)$_2$amino, N,N,N-(C$_{1-10}$alkyl)$_3$ammonio, C$_{1-10}$alkanoylamino, N-(C$_{1-10}$alkyl)carbamoyl, N,N-(C$_{1-10}$alkyl)$_2$carbamoyl, C$_{1-10}$alkylS(O)$_a$ wherein a is 0 to 2, N-(C$_{1-10}$alkyl)sulphamoyl, N,N-(C$_{1-10}$alkyl)$_2$sulphamoyl, N-(C$_{1-10}$alkyl)sulphamoylamino, N,N-(C$_{1-10}$alkyl)$_2$sulphamoylamino, C$_{1-10}$alkoxycarbonylamino, carbocyclyl, carbocyclylC$_{1-10}$alkyl, heterocyclic group, heterocyclylC$_{1-10}$alkyl, carbocyclyl-(C$_{1-10}$alkylene)$_e$-R$^{53}$-(C$_{1-10}$alkylene)$_f$- or heterocyclyl-(C$_{1-10}$alkylene)$_g$-R$^{54}$-(C$_{1-10}$alkylene)$_h$-; wherein R$^{20}$ may be independently optionally substituted on carbon by one or more R$^{57}$; and wherein if said heterocyclyl contains an —NH— group, that nitrogen may be optionally substituted by a group selected from R$^{58}$;

p is 1-3; wherein the values of R$^{15}$ may be the same or different;

q is 0-1;

r is 0-3; wherein the values of R$^{16}$ may be the same or different;

m is 0-2; wherein the values of R$^{12}$ may be the same or different;

n is 1-2; wherein the values of R$^8$ may be the same or different;

z is 0-3; wherein the values of R$^{19}$ may be the same or different;

R$^{21}$ is selected from hydrogen or C$_{1-6}$alkyl;

R$^{22}$ and R$^{23}$ are independently selected from hydrogen, hydroxy, amino, mercapto, C$_{1-6}$alkyl, C$_{1-6}$alkoxy, N-(C$_{1-6}$alkyl)amino, N,N-(C$_{1-6}$alkyl)$_2$amino, C$_{1-6}$alkylS(O)$_a$ wherein a is 0 to 2;

R$^{24}$ is selected from hydrogen, hydroxy, C$_{1-6}$alkyl, C$_{1-4}$alkoxy and C$_{1-6}$alkanoyloxy;

R$^{25}$ is selected from halo, nitro, cyano, hydroxy, amino, carboxy, carbamoyl, mercapto, sulphamoyl, C$_{1-4}$alkyl, C$_{2-4}$alkenyl, C$_{2-4}$alkynyl, C$_{1-4}$alkoxy, C$_{1-4}$alkanoyl, C$_{1-6}$alkanoyloxy, N-(C$_{1-4}$alkyl)amino, N,N-(C$_{1-4}$alkyl)$_2$amino, C$_{1-4}$alkanoylamino, N-(C$_{1-4}$allyl)carbamoyl, N,N-(C$_{1-4}$alkyl)$_2$carbamoyl, C$_{1-4}$alkylS(O)$_a$ wherein a is 0 to 2, C$_{1-4}$alkoxycarbonyl, N-(C$_{1-4}$alkyl)sulphamoyl and N,N-(C$_{1-4}$ alkyl)$_2$sulphamoyl; wherein R$^{25}$, may be independently optionally substituted on carbon by one or more R$^{67}$;

R$^{26}$, R$^{28}$, R$^{30}$, R$^{36}$, R$^{41}$, R$^{47}$, R$^{51}$ and R$^{57}$ are independently selected from halo, nitro, cyano, hydroxy, amino, carbamoyl, mercapto, sulphamoyl, hydroxyaminocarbonyl, C$_{1-10}$alkyl, C$_{2-10}$alkenyl, C$_{2-10}$alkyl, C$_{1-10}$alkoxy, C$_{1-10}$alkanoyl, C$_{1-10}$alkanoyloxy, C$_{1-10}$alkoxycarbonyl, N-(C$_{1-10}$alkyl)amino, N,N-(C$_{1-10}$alkyl)$_2$amino, N,N,N-(C$_{1-10}$alkyl)$_3$ammonio, C$_{1-10}$alkanoylamino, N-(C$_{1-10}$alkyl)carbamoyl, N,N-(C$_{1-10}$alkyl)$_2$carbamoyl, C$_{1-10}$alkylS(O)$_a$ wherein a is 0 to 2, N-(C$_{1-10}$alkyl)sulphamoyl, N)N-(C$_{1-10}$alkyl)$_2$sulphamoyl, N-(C$_{1-10}$alkyl)sulphamoylamino, N,N-(C$_{1-10}$alkyl)$_2$sulphamoylamino, C$_{1-10}$alkoxycarbonylamino, carbocyclyl, carbocyclylC$_{1-10}$alkyl, heterocyclic group, heterocyclyl C$_{1-10}$alkyl, carbocyclyl-(C$_{1-10}$alkylene)$_e$-R$^{59}$-(C$_{1-10}$alkylene)$_f$— or heterocyclyl-(C$_{1-10}$alkylene)$_g$-R$^{60}$-(C$_{1-10}$alkylene)$_h$-; wherein R$^{26}$, R$^{28}$, R$^{30}$, R$^{36}$, R$^{41}$, R$^{47}$, R$^{51}$ and R$^{57}$ may be independently optionally substituted on carbon by one or more R$^{63}$; and wherein if said heterocyclyl contains an —NH— group, that nitrogen may be optionally substituted by a group selected from R$^{64}$;

$R^{27}$, $R^{29}$ $R^{31}$, $R^{37}$, $R^{42}$, $R^{48}$, $R^{52}$, $R^{58}$ and $R^{64}$ are independently selected from $C_{1-6}$alkyl, $C_{1-6}$alkanoyl, $C_{1-6}$alkylsulphonyl, sulphamoyl, N-($C_{1-6}$alkyl)sulphamoyl, N,N-($C_{1-6}$alkyl)$_2$sulphamoyl, $C_{1-6}$alkoxycarbonyl, carbamoyl, N-($C_{1-6}$alkyl)carbamoyl, N,N-($C_{1-6}$alkyl)$_2$carbamoyl, benzyl, phenethyl, benzoyl, phenylsulphonyl and phenyl;

$R^{32}$, $R^{33}$, $R^{43}$, $R^{44}$, $R^{53}$, $R^{54}$, $R^{59}$ and $R^{60}$ are independently selected from —O—, —$NR^{65}$—, —S(O)$_x$—, —$NR^{65}$C(O)$NR^{66}$—, —$NR^{65}$C(S)$NR^{66}$—, —OC(O)N=C—, —$NR^{65}$C(O)— or —C(O)$NR^{65}$—; wherein $R^{65}$ and $R^{66}$ are independently selected from hydrogen or $C_{1-6}$alkyl, and x is 0-2;

$R^{63}$ and $R^{67}$ re independently selected from halo, hydroxy, cyano, carbamoyl, ureido, amino, nitro, carbamoyl, mercapto, sulphamoyl, trifluoromethyl, trifluoromethoxy, methyl, ethyl, methoxy, ethoxy, vinyl, allyl, ethynyl, methoxycarbonyl, formyl, acetyl, formamido, acetylamino, acetoxy, methylamino, dimethylamino, N-methylcarbamoyl, N,N-dimethylcarbamoyl, methylthio, methylsulphinyl, mesyl, N-methylsulphamoyl and N,N-dimethylsulphamoyl; and e, f, g and h are independently selected from 0-2;

or a pharmaceutically acceptable salt, solvate, solvate of such a salt or a prodrug thereof.

Additional suitable IBAT inhibitors having the above structure are selected from any one of:

(+/−)-trans-1,1-dioxo-3-ethyl-3-butyl-5-phenyl-7-methylthio-8-(N-{(R)-α-[N'-(2-(S)-3-(R)-4-(R)-5-(R)-2,3,4,5,6-pentahydroxyhexyl)carbamoyl]benzyl}carbamoylmethoxy)-2,3,4,5-tetrahydro-1,4-benzothiazepine;

(+/−)-trans-1,1-dioxo-3-ethyl-3-butyl-5-phenyl-7-methylthio-8-(N-{(R)-α-[N'-(2-(S)-3-(R)-4-(R)-5-(R)-2,3,4,5,6-pentahydroxyhexyl)carbamoyl]benzyl}carbamoylmethoxy)-2,3,4,5-tetrahydro-1,4-benzothiazepine;

1,1-dioxo-3-ethyl-3-butyl-4-hydroxy-5-phenyl-7-(N-{α[N'-(2-(S)-3-(R)-4-(R)-5-(R)-2,3,4,5,6-pentahydroxyhexyl)carbamoyl]-2-fluorobenzyl}carbamoylmethylthio)-2,3,4,5-tetrahydrobenzothiapine; or 1,1-dioxo-3-butyl-3-ethyl-4-hydroxy-5-phenyl-7-(N-{1-[N-(2-(S)-3-(R)-4-(R)-5-(R)-2,3,4,5,6-pentahydroxyhexyl)carbamoyl]-1-(cyclohexyl)methyl}carbamoylmethylthio)-2,3,4,5-tetrahydrobenzothiepine.

In a particular aspect of the invention an IBAT inhibitor or a pharmaceutically acceptable salt, solvate, solvate of such a salt or a prodrug thereof is an IBAT inhibitor or a pharmaceutically acceptable salt thereof.

Suitable pharmaceutically acceptable salts of the above compounds are, for example, an acid-addition salt of a compound of the invention which is sufficiently basic, for example, an acid-addition salt with, for example, an inorganic or organic acid, for example hydrochloric, hydrobromic, sulphuric, phosphoric, trifluoroacetic, citric, acetate or maleic acid. In addition a suitable pharmaceutically acceptable salt of a compound which is sufficiently acidic is an alkali metal salt, for example a sodium or potassium salt, an alkaline earth metal salt, for example a calcium or magnesium salt, an ammonium salt or a salt with an organic base which affords a physiologically-acceptable cation, for example a salt with methylamine, dimethylamine, trimethylamine, piperidine, morpholine or tris-(2-hydroxyethyl)amine.

The compounds may be administered in the form of a pro-drug which is broken down in the human or animal body to give the parent compound. Examples of pro-drugs include in vivo hydrolysable esters and in vivo hydrolysable amides.

An in vivo hydrolysable ester of a compound containing carboxy or hydroxy group is, for example, a pharmaceutically acceptable ester which is hydrolysed in the human or animal body to produce the parent acid or alcohol. Suitable pharmaceutically acceptable esters for carboxy include $C_{1-6}$alkoxymethyl esters for example methoxymethyl, $C_{1-6}$alkanoyloxymethyl esters for example pivaloyloxymethyl, phthalidyl esters, $C_{3-8}$cycloalkoxycarbonyloxy $C_{1-6}$alkyl esters for example 1-cyclohexylcarbonyloxyethyl; 1,3-dioxolen-2-onylmethyl esters for example 5-methyl-1,3-dioxolen-2-onylmethyl; and $C_{1-6}$alkoxycarbonyloxyethyl esters for example 1-methoxycarbonyloxyethyl and may be formed at any carboxy group in the compounds.

An in vivo hydrolysable ester of a compound containing a hydroxy group includes inorganic esters such as phosphate esters and α-acyloxyalkyl ethers and related compounds which as a result of the in vivo hydrolysis of the ester breakdown to give the parent hydroxy group. Examples of α-acyloxyalkyl ethers include acetoxymethoxy and 2,2-dimethylpropionyloxy-methoxy. A selection of in vivo hydrolysable ester forming groups for hydroxy include alkanoyl, benzoyl, phenylacetyl and substituted benzoyl and phenylacetyl, alkoxycarbonyl (to give alkyl carbonate esters), dialkylcarbamoyl and N-(dialkylaminoethyl)-N-alkylcarbamoyl (to give carbamates), dialkylaminoacetyl and carboxyacetyl. Examples of substituents on benzoyl include morpholino and piperazino linked from a ring nitrogen atom via a methylene group to the 3- or 4-position of the benzoyl ring.

A suitable value for an in vivo hydrolysable amide of a compound containing a carboxy group is, for example, a N-$C_{1-6}$alkyl or N,N-di-$C_{1-6}$alkyl amide such as N-methyl, N-ethyl, N-propyl, N,N-dimethyl, N-ethyl-N-methyl or N,N-diethyl amide.

EXPERIMENTAL

As stated hereinbefore the compounds defined in the present invention are useful in the treatment of functional constipation and C-IBS. These properties may be assessed, for example, using models known in the art:

Buenos dog model for constipation, (Hepato-gasteroenterology, 1980, 27, 381-389). Here dogs are fed with a low fibre/high protein diet to induce constipation;

Niwa's morphine induced constipation model (Bioscience Biotechnology and Biochemistry, 2002, 66, 6, 1233-1240); and Removal of the caecum in rats has also been demonstrated to induce constipation.

Once constipation has been induced the animals can be dosed with an IBAT inhibitor to asses the ability of the IBAT inhibitor to relieve the constipation.

The following data was generated using the Buenos dog model (method described in the publication above) with the modification that the dogs were given 20 g meat/kg dog/day. The result is calculated as mean value of the increase of faeces during the three treatment days subtracted with the entry value (day before start of treatment with the IBAT inhibitor). The dogs were judge as constipation if there faeces amount per day was below 30 gram.

1) Compound 1: 1,1-Dioxo-3,3-dibutyl-5-phenyl-7-methylthio-8-
(N-{(R)-α-[N-(2-sulphoethyl)carbamoyl]-4-
hydroxybenzyl}carbamoylmethoxy)-2,3,4,5-tetrahydro-
1,2,5-benzothiadiazepine

| Substance dosed | No of animals | Dose μmol/kg | Result |
|---|---|---|---|
| Compound 1 | 3 | 5 | 38 ± 7* |
| vehicle only | 3 | 0 | 0 ± 7 |

*Significance <= 0.01

2) Compound 2: 1,1-Dioxo-3,3-dibutyl-5-phenyl-7-methylthio-8-
(N-{(R)-α-[N-((S)-1-carboxy-2-(R)-hydroxypropyl)carbamoyl]-4-
hydroxybenzyl}carbamoylmethoxy)-2,3,4,5-tetrahydro-
1,2,5-benzothiadiazepine

| Substance dosed | No of animals | Dose μmol/kg | Result |
|---|---|---|---|
| Compound 2 | 2 | 1.5 | 23 ± 11 |
| vehicle only | 2 | 0 | −6 ± 3 |

3) Compound 3: 1,1-Dioxo-3,3-dibutyl-5-phenyl-7-methylthio-8-
(N-{(R)-α-[N-((S)-1-carboxy-2-methylpropyl)carbamoyl]-4-
hydroxybenzyl}carbamoylmethoxy)-2,3,4,5-tetrahydro-
1,2,5-benzothiadiazepine

| Substance dosed | No of animals | Dose μmol/kg | Result |
|---|---|---|---|
| Compound 3 | 2 | 1.5 | 39 ± 2* |
| vehicle only | 2 | 0 | 12 ± 2 |

*Significance <= 0.05

The data generated in the Buenos constipated dog model show that all the tested IBAT inhibitors can reverse constipation in this model. The amount of feaces in each dog increased after treatment with compound 1, compound 2 and compound 3 by 38±7, 23±11 and 39±2 g/day, respectively.

According to one aspect of the invention there is provided a pharmaceutical composition which comprises an IBAT inhibitor, or a pharmaceutically acceptable salt, solvate, solvate of such a salt or a prodrug thereof, in association with a pharmaceutically acceptable diluent or carrier for use in the treatment and/or prophylaxis of constipation.

The pharmaceutical compositions may be in a form suitable for oral administration, for example as a tablet or capsule, for parenteral injection (including intravenous, subcutaneous, intramuscular, intravascular or infusion) as a sterile solution, suspension or emulsion, for topical administration as an ointment or cream or for rectal administration as a suppository. In general the above compositions may be prepared in a conventional manner using conventional excipients.

According to another feature of the invention there is provided the use of an IBAT inhibitor, or a pharmaceutically acceptable salt, solvate, solvate of such a salt or a prodrug thereof, in the manufacture of a medicament for use in the treatment and/or prophylaxis of constipation, in a warm-blooded animal, such as man.

Therefore according to the present invention, there is provided a method of treatment and/or prophylaxis of constipation, in a warm-blooded animal, such as man, in need of such treatment and/or prophylaxis which comprises administering to said animal an effective amount of an IBAT inhibitor, or a pharmaceutically acceptable salt, solvate, solvate of such a salt or a prodrug thereof.

According to another feature of the invention there is provided the use of an IBAT inhibitor, or a pharmaceutically acceptable salt, solvate, solvate of such a salt or a prodrug thereof, in the treatment and/or prophylaxis of constipation, in a warm-blooded animal, such as man.

The IBAT inhibitor, or a pharmaceutically acceptable salt, solvate, solvate of such a salt or a prodrug thereof, will normally be administered to a warm-blooded animal at a unit dose within the range 0.5-5000 mg per square meter body area of the animal, i.e. approximately 0.001-50 mg/kg, and this would be expected to provide a therapeutically-effective dose. A unit dose from such as a tablet or capsule will usually contain, for example 0.05-250 mg of active ingredient. In one aspect of the invention a daily dose in the range of 0.01-50 mg/kg is employed. However the daily dose will necessarily be varied depending upon the host treated, the particular route of administration, and the severity of the illness being treated. Accordingly the optimum dosage may be determined by the practitioner who is treating any particular patient.

What we claim is:

1. A method of treating functional constipation or C-IBS, in a warm-blooded animal in need of such treatment, which method comprises administering to said animal an effective amount of an IBAT inhibitor selected from:

1,1-dioxo-3,3-dibutyl-5-phenyl-7-methylthio-8-(N—{(R)-α-[N—((R)-1-carboxy-2-methylthio -ethyl)carbamoyl]-4-hydroxybenzyl}carbamoylmethoxy)-2,3,4,5-tetrahydro-1,2,5-benzothiadiazepine;

1,1-dioxo-3,3-dibutyl-5-phenyl-7-methylthio-8-(N—{(R)-α-[N—((S)-1-carboxy-2-(R)-hydroxypropyl)carbamoyl]-4-hydroxybenzyl}carbamoylmethoxy)-2,3,4,5-tetrahydro-1,2,5-benzothiadiazepine;

1,1-dioxo-3,3-dibutyl-5-phenyl-7-methylthio-8-(N—{(R)-α-[N—((S)-1-carboxy-2-methylpropyl)carbamoyl]-4-hydroxybenzyl}carbamoylmethoxy)-2,3,4,5-tetrahydro-1,2,5-benzothiadiazepine;

1,1-dioxo-3,3-dibutyl-5-phenyl-7-methylthio-8-(N—{(R)-α-[N—((S)-1-carboxybutyl)carbamoyl]-4-hydroxybenzyl}carbamoylmethoxy)-2,3,4,5-tetrahydro-1,2,5-benzothiadiazepine;

1,1-dioxo-3,3-dibutyl-5-phenyl-7-methylthio-8-(N—{(R)-α-[N—((S)-1-carboxypropyl)carbamoyl]benzyl}carbamoylmethoxy)-2,3,4,5-tetrahydro-1,2,5-benzothiadiazepine;

1,1-dioxo-3,3-dibutyl-5-phenyl-7-methylthio-8-(N—{(R)-α-[N—((S)-1-carboxyethyl)carbamoyl]benzyl}carbamoylmethoxy)-2,3,4,5-tetrahydro-1,2,5-benzothiadiazepine;

1,1dioxo-3,3-dibutyl-5-phenyl-7-methylthio-8-(N—{(R)-α-[N—((S)-1-carboxy-2-(R)-hydroxypropyl)carbamoyl]benzyl}carbamoylmethoxy)-2,3,4,5-tetrahydro-1,2,5-benzothiadiazepine;

1,1-dioxo-3,3-dibutyl-5-phenyl-7-methylthio-8-(N—{(R)-α-[N-(2-sulphoethyl)carbamoyl]-4-hydroxybenzyl}carbamoylmethoxy)-2,3,4,5-tetrahydro-1,2,5-benzothiadiazepine;

1,1-dioxo-3,3-dibutyl-5-phenyl-7-methylthio-8-(N—{(R)-α-[N—((S)-1-carboxyethyl)carbamoyl]-4-hydroxybenzyl}carbamoylmethoxy)-2,3,4,5-tetrahydro-1,2,5-benzothiadiazepine;

1,1-dioxo-3,3-dibutyl-5-phenyl-7-methylthio-8-(N—{(R)-α-[N—((R)-1-carboxy-2-methylthioethyl)carbamoyl]benzyl}carbamoylmethoxy)-2,3,4,5-tetrahydro-1,2,5-benzothiadiazepine;

1,1-dioxo-3,3-dibutyl-5-phenyl-7-methylthio-8-(N—
{(R)-α-[N—{(S)-1-[N—((S)-2-hydroxy-1-carboxy-
ethyl)carbamoyl]propyl}carbamoyl]
benzyl}carbamoylmethoxy)-2,3,4,5-tetrahydro-1,2,5-
benzothiadiazepine;

1,1-dioxo-3,3-dibutyl-5-phenyl-7-methylthio-8-(N—
{(R)-α-[N—((S)-1-carboxy-2-methylpropyl)carbam-
oyl]benzyl}carbamoylmethoxy)-2,3,4,5-tetrahydro-1,
2,5-benzothiadiazepine;

1,1-dioxo-3,3-dibutyl-5-phenyl-7-methylthio-8-(N—
{(R)-α-[N—((S)-1-carboxypropyl)  carbamoyl]-4-
hydroxybenzyl}carbamoylmethoxy)-2,3,4,5-tetrahy-
dro-1,2,5-benzothiadiazepine;

1,1-dioxo-3,3-dibutyl-5-phenyl-7-methylthio-8-[N—
((R)-α-carboxy-4-hydroxybenzyl)carbamoyl-
methoxy]-2,3,4,5-tetrahydro-1,2,5-benzothiadiaz-
epine;

1,1-dioxo-3,3-dibutyl-5-phenyl-7-methylthio-8-(N—
{(R)-α-[N-(2-(S)-3-(R)-4-(R)-5-(R)-2,3,4,5,6-pen-
tahydroxyhexyl)carbamoyl]
benzyl}carbamoylmethoxy)-2,3,4,5-tetrahydro-1,2,5-
benzothiadiazepine; and 1,1-dioxo-3,3-dibutyl-5-phenyl-7-methylthio-8-(N—
{(R)-α-[N-(2-(S)-3-(R)-4-(R)-5-(R)-2,3,4,5,6-pen-
tahydroxyhexyl)carbamoyl]-4-
hydroxybenzyl}carbamoylmethoxy)-2,3,4,5-tetrahy-
dro-1,2,5-benzothiadiazepine;

or a pharmaceutically acceptable salt, solvate, solvate of such a salt, or an in vivo hydrolysable ester formed on an available carboxy or hydroxy or an in vivo hydrolysable amide formed on an available carboxy thereof.

2. A method of treating functional constipation or C-IBS, in a warm-blooded animal in need of such treatment, which method comprises administering to said animal an effective amount of an IBAT inhibitor selected from:

1,1-dioxo-3,3-dibutyl-5-phenyl-7-methylthio-8-(N—
{(R)-1'-phenyl-1'-[N'-(carboxymethyl)carbamoyl]
methyl}carbamoylmethoxy)-2,3,4,5-tetrahydro-1,5-
benzothiazepine;

1,1-dioxo-3,3-dibutyl-5-phenyl-7-methylthio-8-(N—
{(R)-α-[N'-(carboxymethyl)carbamoyl]-4-
hydroxybenzyl}carbamoylmethoxy)-2,3,4,5-tetrahy-
dro-1,5-benzothiazepine;

1,1-dioxo-3,3-dibutyl-5-phenyl-7-methylthio-8-(N—
{(R)-1'-phenyl-1'-[N'-(2-sulphoethyl)carbamoyl]
methyl}carbamoylmethoxy)-2,3,4,5-tetrahydro-1,5-
benzothiazepine;

1,1-dioxo-3-butyl-3-ethyl-5-phenyl-7-methylthio-8-(N—
{(R)-1'-phenyl-1'-[N'-(2-sulphoethyl)carbamoyl]
methyl}carbamoylmethoxy)-2,3,4,5-tetahydro-1,5-
benzothiazepine;

1,1-dioxo-3,3-dibutyl-5-phenyl-7-methylthio-8-(N—
{(R)-α-[N'-(2-sulphoethyl)carbamoyl]-4-
hydroxybenzyl}carbamoylmethoxy)-2,3,4,5-tetrahy-
dro-1,5-benzothiazepine;

1,1-dioxo-3-butyl-3-ethyl-5-phenyl-7-methylthio-8-(N—
{(R)-α-[N'-(2-sulphoethyl)carbamoyl]-4-
hydroxybenzyl}carbamoylmethoxy)-2,3,4,5-tetrahy-
dro-1,5-benzothiazepine;

1,1-dioxo-3-butyl-3-ethyl-5-phenyl-7-methylthio-8-(N—
{(R)-α-[N'-(2-carboxyethyl)carbamoyl]
benzyl}carbamoylmethoxy)-2,3,4,5-tetrahydro-1,5-
benzothiazepine;

1,1-dioxo-3,3-dibutyl-5-phenyl-7-methylthio-8-(N—
{(R)-α-[N'-(2-carboxyethyl)carbamoyl]-4-
hydroxybenzyl}carbamoylmethoxy)-2,3,4,5-tetrahy-
dro-1,5-benzothiazepine;

1,1-dioxo-3-butyl-3-ethyl-5-phenyl-7-methylthio-8-(N—
{(R)-α-[N'-(5-carboxypentyl)carbamoyl]
benzyl}carbamoylmethoxy)-2,3,4,5-tetrahydro-1,5-
benzothiazepine;

1,1-dioxo-3,3-dibutyl-5-phenyl-7-methylthio-8-(N—
{(R)-α-[N'-(2-carboxyethyl)carbamoyl]
benzyl}carbamoylmethoxy)-2,3,4,5-tetrahydro-1,5-
benzothiazepine;

1,1-dioxo-3,3-dibutyl-5-phenyl-7-methylthio-8-(N-{α-
[N'-(2-sulphoethyl)carbamoyl]-2-
fluorobenzyl}carbamoylmethoxy)-2,3,4,5-tetrahydro-
1,5-benzothiazepine;

1,1-dioxo-3-butyl-3-ethyl-5-phenyl-7-methylthio-8-(N—
{(R)-α-[N'-(R)-(2-hydroxy-1-carboxyethyl)carbam-
oyl]benzyl}carbamoylmethoxy)-2,3,4,5-tetrahydro-1,
5-benzothiazepine;

1,1-dioxo-3,3-dibutyl-5-phenyl-7-methylthio-8-(N{(R)-
α-[N'-(R)-(2-hydroxy-1-carboxyethyl)carbamoyl]
benzyl}carbamoylmethoxy)-2,3,4,5-tetrahydro-1,5-
benzothiazepine;

1,1-dioxo-3,3-dibutyl-5-phenyl-7-methylthio-8-{N—
[(R)-α-(N'—{(R)-1-[N'—(R)-(2-hydroxy-1-carboxy-
ethyl)carbamoyl]-2-hydroxyethyl}carbamoyl)benzyl]
carbamoylmethoxy}-2,3,4,5-tetrahydro-1,5-
benzothiazepine;

1,1-dioxo-3-butyl-3-ethyl-5-phenyl-7-methylthio-8-(N-
{α-[N'-(carboxymethyl)carbamoyl]
benzyl}carbamoylmethoxy)-2,3,4,5-tetrahydro-1,5-
benzothiazepine;

1,1-dioxo-3-butyl-3-ethyl-5-phenyl-7-methylthio-8-(N-
{α-[N'-((ethoxy)(methyl)phosphorylmethyl)carbam-
oyl]benzyl}carbamoylmethoxy)-2,3,4,5-tetrahydro-1,
5-benzothiazepine;

1,1-dioxo-3-butyl-3-ethyl-5-phenyl-7-methylthio-8-{N—
[(R)-α-(N'-{2-[(hydroxy)(methyl)phosphoryl]
ethyl}carbamoyl)benzyl]carbamoylmethoxy}-2,3,4,5-
tetrahydro-1,5-benzothiazepine;

1,1-dioxo-3,3-dibutyl-5-phenyl-7-methylthio-8-(N—
{(R)-α-[N'-(2-methylthio-1-carboxyethyl)carbamoyl]
benzyl}carbamoylmethoxy)-2,3,4,5-tetrahydro-1,5-
benzothiazepine;

1,1-dioxo-3,3-dibutyl-5-phenyl-7-methylthio-8-{N—
[(R)-α-(N'-{2-[(methyl)(ethyl)phosphoryl]
ethyl}carbamoyl)-4-hydroxybenzyl]carbamoyl-
methoxy}-2,3,4,5-tetrahydro-1,5-benzothiazepine;

1,1-dioxo-3,3-dibutyl-5-phenyl-7-methylthio-8-{N—
[(R)-α-(N'-{2-[(methyl)(hydroxy)phosphoryl]
ethyl}carbamoyl)-4-hydroxybenzyl]carbamoyl-
methoxy}-2,3,4,5-tetrahydro-1,5-benzothiazepine;

1,1-dioxo-3,3-dibutyl-5-phenyl-7-methylthio-8-(N—
{(R)-α-[(R)—N'-(2-methylsulphinyl-1-carboxyethyl)
carbamoyl]benzyl}carbamoylmethoxy)-2,3,4,5-tet-
rahydro-1,5-benzothiazepine;

1,1-dioxo-3,3-dibutyl-5-phenyl-7-methoxy-8-[N—{(R)-
α-[N'-(2-sulphoethyl)carbamoyl]-4-
hydroxybenzyl}carbamoylmethoxy]-2,3,4,5-tetrahy-
dro-1,5-benzothiazepine;

1,1-dioxo-3,3-dibutyl-5-phenyl-7-methylthio-8-(N—
{(R)-α-[N'-(2-(S)-3-(R)-4-(R)-5-(R)-2,3,4,5,6-pen-
tahydroxyhexyl)carbamoyl]
benzyl}carbamoylmethoxy)-2,3,4,5-tetrahydro-1,5-
benzothiazepine;

1,1-dioxo-3-butyl-3-ethyl-5-phenyl-7-methylthio-8-(N—
{(R)-α-[N'-(2-(S)-3-(R)-4-(R)-5-(R)-2,3,4,5,6-pen-
tahydroxyhexyl)carbamoyl]
benzyl}carbamoylmethoxy)-2,3,4,5-tetrahydro-1,5-
benzothiazepine;

1,1-dioxo-3-butyl-3-ethyl-5-phenyl-7-methylthio-8-(N—{(R)-α-[N'—((S)-1-carbamoyl-2-hydroxyethyl)carbamoyl]benzyl}carbamoylmethoxy)-2,3,4,5-tetrahydro-1,5-benzothiazopine;

1,1-dioxo-3-butyl-3-ethyl-5-phenyl-7-methylthio-8-(N—{(R)-α-[N'-(hydroxycarbomoyl-methyl)carbamoyl]benzyl}carbamoylmethoxy)-2,3,4,5-tetrahydro-1,5-benzothiazepine;

1,1-dioxo-3-butyl-3-ethyl-5-phenyl-7-methylthio-8-[N—((R)-α-{N'-[2-(N'-pyrimidin-2-ylureido)ethyl]carbamoyl}benzyl)carbamoylmethoxy]-2,3,4,5-tetrahydro-1,5-benzothiazepine;

1,1-dioxo-3-butyl-3-ethyl-5-phenyl-7-methylthio-8-[N—((R)-α-{N'-[2-(N'-pyridin-2-ylureido)ethyl]carbamoyl}benzyl)carbamoylmethoxy]-2,3,4,5-tetrahydro-1,5-benzothiazepine;

1,1-dioxo-3-butyl-3-ethyl-5-phenyl-7-methylthio-8-(N—{(R)-α-[N'-(1-3-butoxycarbonylpiperidin-4-ylmethyl)carbamoyl]benzyl}carbamoylmethoxy)-2,3,4,5-tetrahydro-1,5-benzothiazepine;

1,1-dioxo-3-butyl-3-ethyl-5-phenyl-7-methylthio-8-(N{(R)-α-[N'-(2,3-dihydroxypropyl)carbamoyl]benzyl}carbamoylmethoxy)-2,3,4,5-tetrahydro-1,5-benzothiazepine;

1,1-dioxo-3-butyl-3-ethyl-5-phenyl-7-methylthio-8-[N—((R)-α-{N'-[2-(3,4-dihydroxyphenyl)-2-methoxyethyl]carbamoyl}benzyl)carbamoylmethoxy]-2,3,4,5-tetrahydro-1,5-benzothiazepine;

1,1-dioxo-3-butyl-3-ethyl-5-phenyl-7-methylthio-8-(N—{(R)-α-[N-(2-aminoethyl)carbamoyl]benzyl}carbamoylmethoxy)2,3,4,5-tetrahydro-1,5-benzothiazepine;

1,1dioxo-3-butyl-3-ethyl-5-phenyl-7-methylthio-8-(N—{(R)-α-[N'-(piperidin-4-ylmethyl)carbamoyl]benzyl}carbamoylmethoxy)-2,3,4,5-tetrahydro-1,5-benzothiazepine; and 1,1-dioxo-3-butyl-3-ethyl-5-phenyl-7-methylthio-8-(N—{(R)-α-[N-(2-N,N-dimethylaminosulphamoylethyl)carbamoyl]benzyl}carbamoylmethoxy)-2,3,4,5-tetrahydro-1,5-benzothiazepine;

or a pharmaceutically acceptable salt, solvate, solvate of such a salt, or an in vivo hydrolysable ester formed on an available carboxy or hydroxy or an in vivo hydrolysable amide formed on an available carboxy thereof.

3. The method according to claim 1 or claim 2 for the treatment of functional constipation.

4. The method according to claim 1 or claim 2 for the treatment of C-IBS.

* * * * *